(12) United States Patent
O'Hare et al.

(10) Patent No.: US 10,035,878 B2
(45) Date of Patent: Jul. 31, 2018

(54) LACTIDE POLYMERISATION

(71) Applicant: SCG Chemicals Co., Ltd., Bangkok (TH)

(72) Inventors: Dermot O'Hare, Oxford (GB);
Jean-Charles Buffet, Oxford (GB);
Zoe Turner, Oxford (GB)

(73) Assignee: SCG Chemicals Co., Ltd., Bangkok (TH)

(*) Notice: Subject to any disclaimer, the term of this patent is extended or adjusted under 35 U.S.C. 154(b) by 0 days.

(21) Appl. No.: 15/302,581

(22) PCT Filed: Apr. 8, 2015

(86) PCT No.: PCT/EP2015/057851
§ 371 (c)(1),
(2) Date: Oct. 7, 2016

(87) PCT Pub. No.: WO2015/155214
PCT Pub. Date: Oct. 15, 2015

(65) Prior Publication Data
US 2017/0022320 A1 Jan. 26, 2017

(30) Foreign Application Priority Data
Apr. 9, 2014 (GB) .................................. 1406406.7

(51) Int. Cl.
*C08G 63/82* (2006.01)
*C08G 63/08* (2006.01)
(Continued)

(52) U.S. Cl.
CPC .............. *C08G 63/823* (2013.01); *C07F 7/00* (2013.01); *C07F 7/222* (2013.01); *C07F 7/28* (2013.01);
(Continued)

(58) Field of Classification Search
None
See application file for complete search history.

(56) References Cited

U.S. PATENT DOCUMENTS

| 2005/0009687 A1 | 1/2005 | Verkade et al. |
| 2006/0111527 A1* | 5/2006 | Damrau ............ C07F 17/00 526/170 |
| 2008/0249255 A1 | 10/2008 | Asandei |

FOREIGN PATENT DOCUMENTS

| CN | 1566170 A | 1/2005 |
| EP | 0749985 A2 | 12/1996 |

(Continued)

OTHER PUBLICATIONS

Obora et al., "Dehydrocoupling polymerization of arylsilanes with chloro(aryloxy)bis(cyclopentadienyl)zirconium complex catalysts," J. Org. Chem. 595 (2000), 1-11 (Year: 2000).*

(Continued)

*Primary Examiner* — Catherine S Branch
(74) *Attorney, Agent, or Firm* — Foley Hoag LLP

(57) ABSTRACT

The present invention relates to a compound having the formula $L_aM(OR^1)_bR^2_cX_d$ wherein M is a metal selected from Ti, Zr and Hf; L is a ligand selected from permethylpentalene, (hydro)permethyl-pentalene, (hydro)pentalene, cyclopentadiene, indene and ethylene- or silane-bridged indene, preferably (bis)indene; $R^1$ is a 1-6C alkyl, substituted or unsubstituted phenyl, or a substituted or unsubstituted phenylalkylene group; $R^2$ is Me or Et; X is halogen; a=1 to 3, b=1 to 3, c=0 or 1 and d=0, 1, 2 or 3; and dimers thereof, the use of the compound as an initiator in the polymerization of lactide monomer and a process for producing a polylactide performed by contacting a lactide monomer with the compound.

14 Claims, 7 Drawing Sheets

Figure 1:
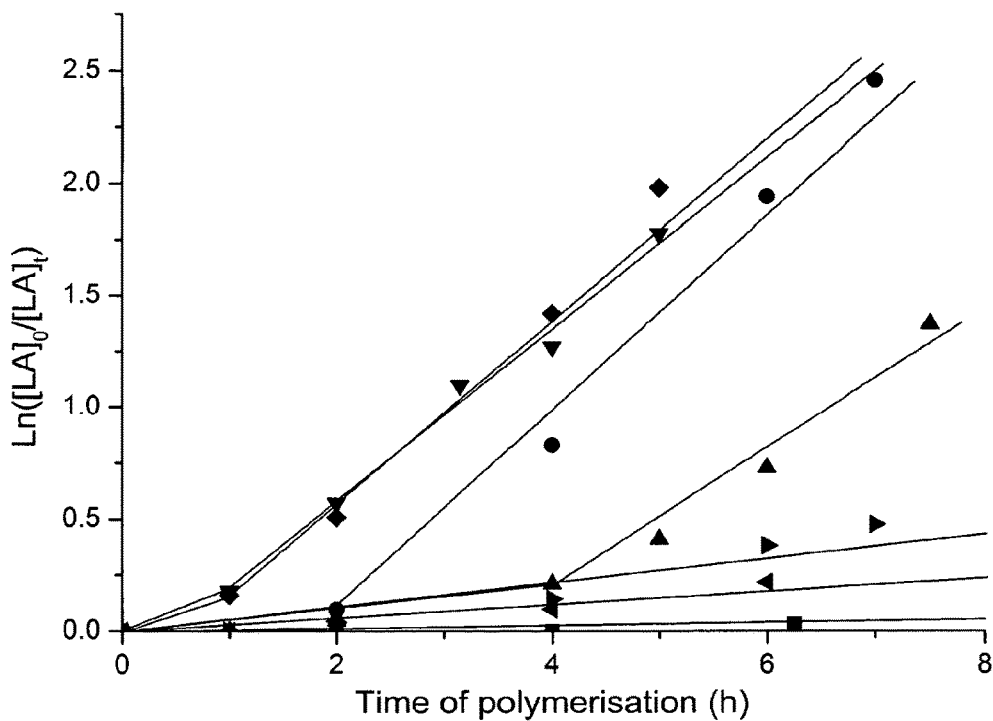

(51) Int. Cl.
    *C07F 7/00*     (2006.01)
    *C07F 7/28*     (2006.01)
    *C07F 7/22*     (2006.01)
    *C08G 65/336*     (2006.01)
    *C09J 201/10*     (2006.01)
    *C08L 101/10*     (2006.01)
    C08G 77/00     (2006.01)

(52) U.S. Cl.
    CPC ........... *C08G 63/08* (2013.01); *C08G 65/336* (2013.01); *C08L 101/10* (2013.01); *C09J 201/10* (2013.01); *C08G 77/70* (2013.01)

(56) References Cited

FOREIGN PATENT DOCUMENTS

| | | |
|---|---|---|
| EP | 0897926 A1 | 2/1999 |
| JP | 2005/126627 A | 5/2005 |
| JP | 2012/153795 A | 8/2012 |
| WO | WO-2006/065809 A2 | 6/2006 |
| WO | WO-2008/110774 A2 | 9/2008 |
| WO | WO-2015/155214 A2 | 10/2015 |

OTHER PUBLICATIONS

Hsiao, et al., "Stereoregular Diblock Copolymers of Syndiotactic Polystyrene Derivatives and Polylactide: Syntheses and Self-Assembled Nanostructures," Macromolecules, 44: 286-298 (2011).

International Search Report and Written Opinion for International Application No. PCT/EP2015/057581 dated Dec. 22, 2015.

Jonas, et al., "Mononuclear pentalene and methylpentalene complexes of titanium, zirconium, and hafnium," Angewandte Chemie International Ed, 36(16): 1714-1718 (1997).

Kim, et al., "Titanium Alkoxides as initiators for the controlled polymerization of lactide," Inorg Chem, 42(5): 1437-1447 (2003).

Li, et al., "Mononuclear bis(pentalene) sandwich compounds of the first-row transition metals: variable hapticity of the pentalene rings and intramolecular coupling reactions," New J Chem, 35(8): 1718-1729 (2011).

Mami, et al., "Injection-molded products of ethylene polymer compositions with excellent balance of impact strength and elongation," Machine Translation of JP 2012/153795.

Metz, et al., "Weakly coordinating Al-, Nb-, Ta-, Y-, and La-based perfluoroaryloxymetalate anions as cocatalyst components for single-site olefin polymerization," Organometallics, 21(18): 3691-3702 (2002).

Okane, et al., "Addition polymerization catalysts and manufacture of polymers with high molecular weight using them," Machine Translation of JP 2005/126627.

Okuda, et al., "Indenyl effect in d 0-transition metal complexes: synthesis, molecular structure and lactone polymerization activity of [Ti([eta]5-C9H7)Cl2(OMe)]," J Organomet Chem, 501(1-2): 37-39 (1995).

Petzetakis, et al., "Titanium-mediated [CpTiCl 2 (OEt)] ring-opening polymerization of lactides: A novel route to well-defined polylactide-based complex macromolecular architectures," J Polym Sci A1, 48(5): 1092-1103 (2010).

Priftis, et al., "Surface-Initiated Titanium-Mediated Coordination Polymerization from Catalyst-Functionalized Single and Multiwalled Carbon Nanotubes," Macromolecules, 42: 3340-3346 (2009).

Saridis, et al., "-lactide using half-tilanocene complexes of the ATiCl 2 Nu type: Synthesis, characterization, and thermal properties," J Polym Sci A1, 51(5): 1162-1174 (2013).

* cited by examiner

LACTIDE POLYMERISATION

RELATED APPLICATIONS

This application is a § 371 national stage application based on Patent Cooperation Treaty Application serial number PCT/EP2015/057581, filed Apr. 8, 2015, which claims the benefit of priority to GB 1406406.7, filed Apr. 9, 2014.

The present invention relates to the production of poly (lactic acids). It, further, relates to metal complexes that are useful as catalysts/initiators in lactide polymerisation.

Poly(lactic acids) (PLAs) have been studied intensely during the past few decades because of their biodegradability and biocompatibility. PLA possesses versatile physical properties and has been used in medical applications and tissue engineering such as media for controlled drug release. Ring opening polymerisation (ROP) of lactide (LA) by single-site initiators is the most efficient route to PLAs with controlled molecular weight and narrow molecular weight distribution. The two stereogenic centres in one lactide molecule results in three distinct configurational isomers (S,S)-LA, (L-LA); (R,R)-LA, (D-LA) and (R,S)-LA, (meso)-LA. The 1:1 mixture of (S,S)-LA and (R, R)-LA is referred to as rac-LA.

Metal complexes useful for initiating ring opening polymerisation of lactides are known.

Wenshan Ren et al, Inorganic Chemistry Communications, 30, (2013), 26-28 report that benzyl thorium metallocenes [$\eta^5$-1,3-(Me$_3$C)$_2$C$_5$H$_3$]$_2$Th(CH$_2$Ph)$_2$ (1) and [$\eta^5$-1,2,4-(Me$_3$C)$_3$CH$_2$H$_2$]$_2$Th(CH$_2$Ph)$_2$ (2) can initiate the ring opening polymerisation (ROP) of racemic-lactide (rac-LA) under mild conditions. Complete conversion of 500 equiv of lactide occurs within 5 h at 40° C. in dichloromethane at [rac-LA]=1.0 mol L$^{-1}$, and the molecular weight distribution is very narrow (ca.1.15) over the entire monomer-to-initiator range, indicating a single-site catalyst system.

Yalan Ning et al, Organometallics 2008, 27, 5632-5640 report four neutral zirconocene bis(ester enolate) and non-zirconocene bis(alkoxy) complexes employed for ring-opening polymerisations and chain transfer polymerisations of L-lactide (L-LA) and ε-caprolactone (ε-CL).

A J Chmura et al, Chem. Commun. 2008, 1293, found that zirconium and hafnium amine tris(phenolate) alkoxides are extremely active, yielding highly heterotactic polylactide.

The present invention is based on the discovery of a different class of compounds which have use as initiators for the polymerisation of lactide monomers.

The present invention provides a compound having the formula $$L_aM(OR^1)_bR^2{}_cX_d$$

wherein
M is a metal selected from Ti, Zr and Hf;
L is a ligand selected from permethylpentalene (Pn*=C$_8$Me$_6$), (hydro)permethylpentalene(Pn*(H)=C$_8$Me$_6$H), (hydro)pentalene (Pn(H)=C$_8$H$_8$), cyclopentadiene (Cp=C$_5$H$_5$), indene (C$_7$H$_7$) and ethylene- or silane-bridged indene;
R$^1$ is a 1-6 C alkyl, substituted or unsubstituted phenyl, or a substituted or unsubstituted phenylalkylene group;
R$^2$ is Me or Et
X is halogen
a=1 to 3, b=1 to 3, c=0 or 1 and d=0, 1, 2 or 3
and dimers thereof.

Pentalenes, referred to above, have the structures shown below:

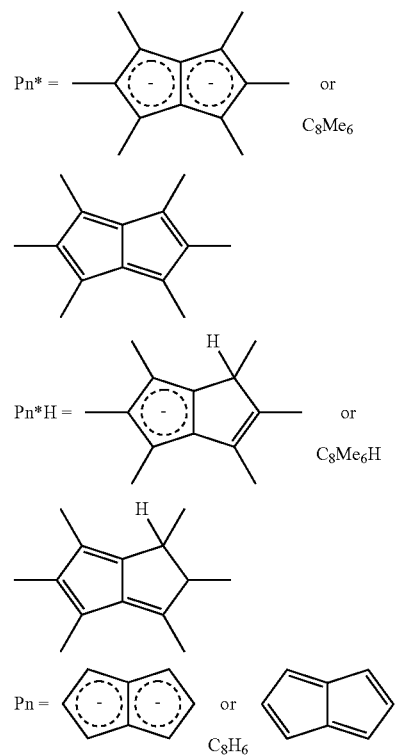

The silane-bridge can be optionally substituted with a range of alkyl groups. The SBI ligand refers to the di-methyl silane bridged indenyl ligand.

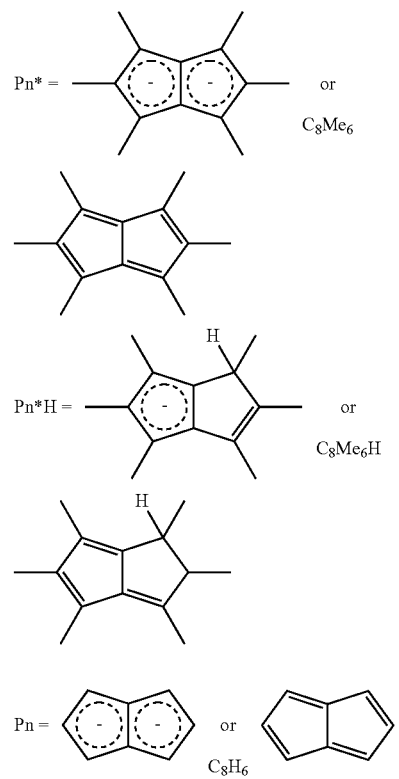

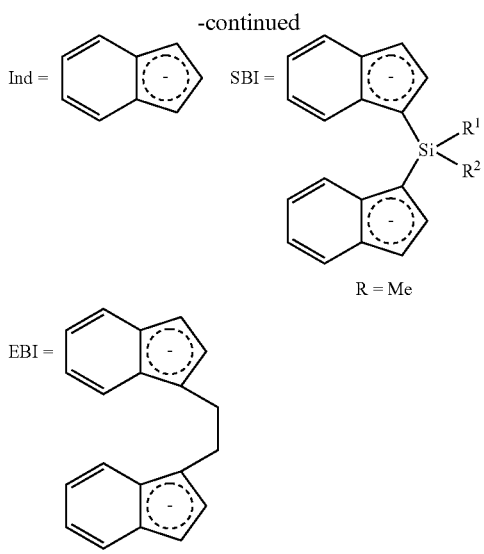

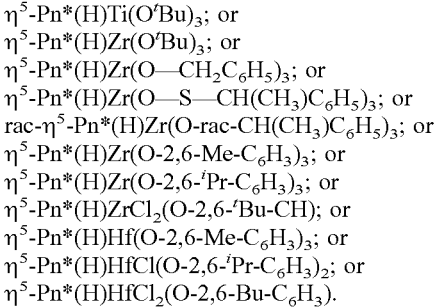

R = Me

The present invention, further, provides the use of a compound of the invention as an initiator in the polymerisation of a lactide monomer.

The present invention, yet further, provides a process for producing a polylactide which comprises contacting a lactide monomer with a compound of the invention.

As stated above, compounds of the present invention have the general formula

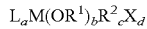

where L, M, $R^1$, $R^2$, X, a, b, c and d are as defined above, and dimers thereof.

M is a Group IV transition metal selected from titanium, zirconium and hafnium. According to one preferred embodiment, M is titanium. According to another preferred embodiment, M is zirconium. According to a different embodiment, M is hafnium.

L is a ligand selected from permethylpentalene(Pn*), (hydro)permethylpentalene(Pn*(H)), (hydro)pentalene(Pn (H)), cyclopentadiene (Cp), indene and ethylene-bridged indene (EBI) and dimethylsilane-bridged indene (SBI). According to one preferred embodiment, the ligand group L is permethylpentalene. According to a different embodiment, the ligand group L is indene or EBI when M is Zr.

The compounds of the present invention are alkoxide, phenyloxide or phenylalkyleneoxide metal complexes based on the ligand group L. $R^1$ of the $OR^1$ group attached to the metal M is selected from 1-6C alkyl, substituted or unsubstituted phenyl and substituted or unsubstituted phenylalkylene. Preferably, the 1-6C alkyl group, for $R^1$, is a tertiary butyl group. Preferably, when $R^1$ is a phenyloxide group, it is a dialkylphenyloxide group of the formula —$C_6H_3(R^3)_2$ where $R^3$ is a 1-4C alkyl group, especially Me, $^iPr$ or $^tBu$. According to a preferred embodiment, $R^1$ is selected from 2,6-dimethylphenyl, 2,6-diisopropylphenyl and 2,6-ditertiarybutylphenyl.

$R^1$ may, according to a different embodiment, be a substituted or unsubstituted phenylalkylene group as mentioned above. Examples include —$CH_2C_6H_5$ and —$CH(Me)C_6H_5$.

The metal complexes of the invention may contain one $R^2$ group attached to the metal M. If present, $R^2$ is selected from Me and Et. If $R^2$ is present in the complex, it is preferably methyl.

The metal complexes of the invention may contain a halogen group X attached to M. Preferably, if present, X is Cl. Typically, if X is present in the complex, the value of d is 1 or 2.

According to a preferred embodiment, the compound of the invention is a (half)metallocene complex being $\eta^5$-Pn*(H)Ti(O$^t$Bu)$_3$; or
$\eta^5$-Pn*(H)Zr(O$^t$Bu)$_3$; or
$\eta^5$-Pn*(H)Zr(O—CH$_2$C$_6$H$_5$)$_3$; or
$\eta^5$-Pn*(H)Zr(O—S—CH(CH$_3$)C$_6$H$_5$)$_3$; or
rac-$\eta^5$-Pn*(H)Zr(O-rac-CH(CH$_3$)C$_6$H$_5$)$_3$; or
$\eta^5$-Pn*(H)Zr(O-2,6-Me-C$_6$H$_3$)$_3$; or
$\eta^5$-Pn*(H)Zr(O-2,6-$^i$Pr-C$_6$H$_3$)$_3$; or
$\eta^5$-Pn*(H)ZrCl$_2$(O-2,6-$^t$Bu-CH); or
$\eta^5$-Pn*(H)Hf(O-2,6-Me-C$_6$H$_3$)$_3$; or
$\eta^5$-Pn*(H)HfCl(O-2,6-$^i$Pr-C$_6$H$_3$)$_2$; or
$\eta^5$-Pn*(H)HfCl$_2$(O-2,6-Bu-C$_6$H$_3$).

The compounds above may be made, for instance, by the reaction of $\eta^5$-Pn*(H)SnMe$_3$ with the corresponding metal chloride, e.g. TiCl$_4$, ZrCl$_4$ or HfCl$_4$, in benzene at 80° C. for 2-72 h and then with the appropriate potassium alkoxide, potassium phenyloxide or potassium phenylalkyleneoxide at room temperature in benzene or toluene. However, any suitable process for preparing the compounds known in the art may be used for preparation thereof.

According to a different preferred embodiment, the (half) metallocene complex of the invention is

[(Pn*)Ti(O-2,6-Me-C$_6$H$_3$)Cl]; or
[$\eta^8$-(Pn*)Ti(O-2,4-$^t$Bu-C$_6$H$_3$)Cl]; or
[$\eta^8$-(Pn*)Ti(O-2,6-Me-C$_6$H$_3$)$_2$]; or
[$\eta^8$-(Pn*)Ti(O$^t$Bu)Cl]; or
[$\eta^8$-(Pn*)Ti(O$^t$Bu)$_2$; or
[$\eta^5$-(Pn*H)Ti(O-2,6-Me-C$_6$H$_3$)Cl$_2$]; or
[$\eta^5$-(Pn*H)Ti(O-2,6-Me-C$_6$H$_3$)$_3$].

The above compounds may be produced, for example, by the reaction of one equivalent of [$\eta^8$-(Pn*)TiCl($\mu$-Cl)]$_2$ with two equivalents of KOR (where R=2,6-MeC$_6$H$_3$ or 2,4-$^t$BuC$_6$H$_3$) at room temperature in toluene for 24-48 h. However, any suitable process for preparing the compounds known in the art may be used for preparation thereof.

According to yet a further preferred embodiment, the (half)metallocene complex of the invention is

[(EBI)Zr(O-2,6-Me-C$_6$H$_3$)Cl]; or
[Ind$_2$Zr(O-2,6-Me-C$_6$H$_3$)Me]; or
[Ind$_2$Zr(O-2,6-Me-C$_6$H$_3$)Cl]; or
[Ind$_2$Zr(O-2,6-Me-C$_6$H$_3$)$_2$]; or
[Cp$_2$Zr(O-2,6-Me-C$_6$H$_3$)$_2$]; or
[Cp$_2$Zr(O-2,6-Me-C$_6$H$_3$)Cl]; or
[Cp$_2$Zr(O-2,6-Me-C$_6$H$_3$)Me].

The above EBI Zr compounds may be produced by reacting stoichiometric amounts of [K(O-2,6-Me-C$_6$H$_3$)] and rac-[(EBI)ZrCl$_2$] in toluene with stirring for 18 h at room temperature. A modified procedure for preparing [(Ind)$_2$Zr(O$^t$Bu)Me] involves reacting stoichiometric amounts of [(Ind)$_2$ZrMe$_2$] and tert-butanol in toluene with stirring at room temperature for 18 h, followed by concentration in vacuum. [(Ind)$_2$Zr(O-2,6-Me-C$_6$H$_3$)Me] can be prepared by reacting stoichiometric amounts of [(Ind)$_2$ZrMe] and 2,6-dimethylphenol in toluene with stirring at room temperature for 18 h, followed by concentration in vacuo. However, any suitable process for preparing the compounds known in the art may be used for preparation thereof.

The compounds of the invention are useful as initiators in the polymerisation of a lactide monomer. Accordingly, the present invention also relates to the use of a compound as hereinbefore described as an initiator in the polymerisation of a lactide monomer.

According to a further aspect, the invention provides a process for producing a polylactide which comprises contacting a lactide monomer with a compound as hereinbefore described.

In a preferred embodiment of the process, the lactide monomer is L-lactide and the resulting polylactide is isotactic polylactide. In another preferred embodiment of the process, the lactide monomer is rac-lactide and the resulting polylactide is atactic polylactide.

Experimental Detail I—Relating to Permethylpentalenes

General Procedure

All organometallic syntheses were performed under an inert atmosphere of nitrogen gas, utilizing standard Schlenk techniques on a dual vacuum-inlet gas manifold or Braun glove box. Where necessary, solvents were dried SPS drying system (hexane, pentane, toluene). Deuterated NMR solvents were dried over NaK (benzene-$d_6$, toluene-$d_8$) or $CaH_2$ (chloroform-$d_1$), vacuum transferred and free-pump-thaw-degassed three times prior to use. Elemental analyses were conducted by Mr Stephen Boyer at the elemental analysis service at London Metropolitan University. NMR spectra were recorded using Young's tap NMR tubes on a Varian Mercury VX-Works 300 MHz spectrometer. $^1H$ and $^{13}C\{^1H\}$ NMR spectra were referenced via the residual protio-solvent peak. Potassium tert-butoxide was purchased from Sigma-Aldrich and used as received. L- and rac-lactide were purchased from Alfa Aesar and re-crystallized and sublimed ($10^{-2}$ mbar, 50° C.) prior to use. [K(O-2,6-Me-$C_6H_3$)] and [K(O-2,4-$^t$Bu-$C_6H_3$)] were prepared by stirring potassium bis(trimethylsilyl)amide with the appropriate alcohol in THF at room temperature.

X-ray Crystallography

Crystals were mounted on glass fibres using perfluoropolyether oil, transferred to a goniometer head on the diffractometer and cooled rapidly to 150K in a stream of cold nitrogen using an Oxford Cryosystems CRYOSTREAM unit. Data collections were performed using an Enraf-Nonium FR590 KappaCCD diffractometer, utilising graphite-monochromated Mo $K_\alpha$ X-ray radiation ($\lambda$=0.71073 Å). Intensity data were processed using the DENZO-SMN package. Structures were solved using the direct-methods program SIR92, and refined using full-matrix least squares refinement on all $F^2$ data using the CRYSTALS program suite.

Polymerisation Procedure

All polymerizations were carried out in Young's tap NMR tubes containing 0.4 mL of a benzene-$d_6$ solution of lactide with an initial lactide concentration of $[LA]_0$=0.104 M and 0.1 mL of a benzene-$d_6$ solution of catalyst (of a concentration to ensure $[LA]_0/[init.]_0$=50). Lactide conversion was subsequently calculated by comparing the integration values of the methane signal of PLA and lactide monomer in the $^1H$ NMR spectrum. The temperature at which a given polymerisation was carried out varied in the temperature range 80 to 100° C. and is noted in the appropriate section.

Further advantages and features of the subject-matter of the present invention can be taken from the following detailed description taking in conjunction with the drawing, in which:

FIG. 1: L-lactide polymerization using the complexes: $\eta^5$-Pn*(H)Ti(O-2,6-Me$_2$C$_6$H$_3$)$_3$, 2 (black square, $k_{obs}$=0.113±0.014 h$^{-1}$), $\eta^5$-Pn*(H)Zr(O-2,6-Me$_2$C$_6$H$_3$)$_3$, 7 (red circle, $k_{obs}$=0.479±0.032 h$^{-1}$), $\eta^5$-Pn*(H)Zr(O-2,6-$^i$Pr$_2$C$_6$H$_3$)$_3$, 8 (pink triangle, $k_{obs}$=0.391±0.022 h$^{-1}$), $\eta^5$-Pn*(H)ZrCl$_2$(O-2,6-$^t$Bu$_2$C$_6$H$_3$), 9 (dark blue triangle, $k_{obs}$=0.043±0.003 h$^{-1}$), $\eta^5$-Pn*(H)Hf(O-2,6-Me$_2$C$_6$H$_3$)$_3$, 10 (blue triangle, $k_{obs}$=0.364±0.027 h$^{-1}$), $\eta^5$-Pn*(H)HfCl(O-2,6-$^i$Pr$_2$C$_6$H$_3$)$_2$, 11 (green losange, $k_{obs}$=0.463±0.029 h$^{-1}$) and $\eta^5$-Pn*(H)HfCl$_2$(O-2,6-$^t$BuC$_6$H$_3$), 12 (purple triangle, $k_{obs}$=0.086±0.020 h$^{-1}$). Polymerisation conditions:chloroform-$d_1$ at 100° C. with $[LA]_0/[M]_0$=50, $[LA]_0$=0.5M.

Figure 2:
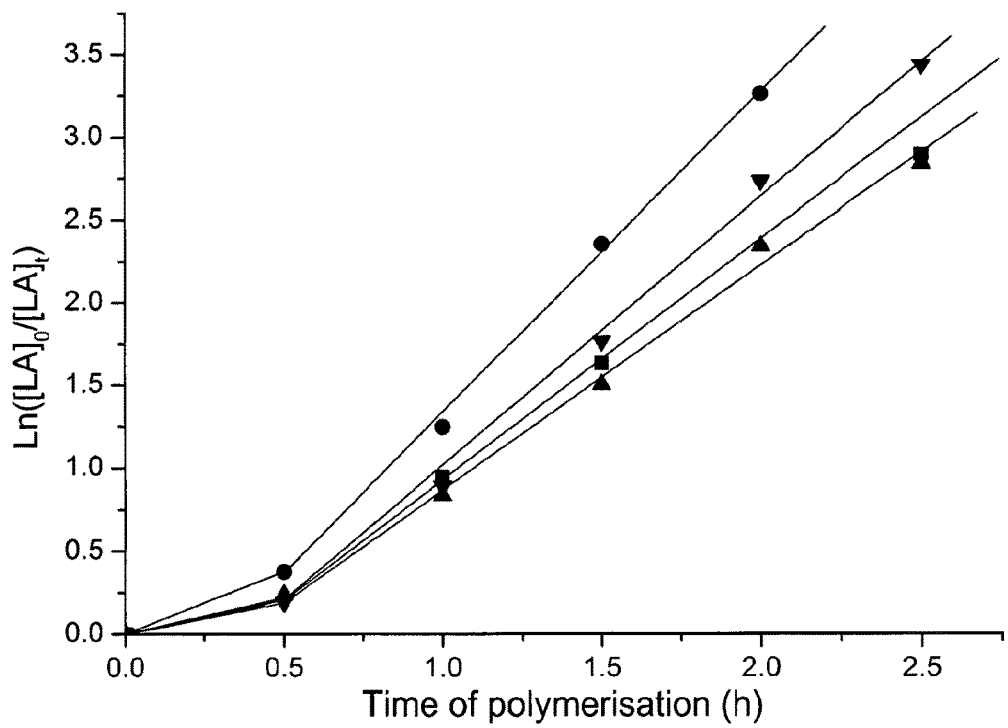

FIG. 2: Lactide polymerisation: L-lactide and S-$\eta^5$-Pn*(H)Zr(O—CH{CH$_3$}C$_6$H$_5$)$_3$, 5 (black square, $k_{obs}$=1.166±0.068 h$^{-1}$); L-lactide and rac-$\eta^5$-Pn*(H)Zr(O—CH{CH$_3$}C$_6$H$_5$)$_3$, 6 (red circle, $k_{obs}$=1.954±0.063 h$^{-1}$); rac-lactide and rac-$\eta^5$-Pn*(H)Zr(O—CH{CH$_3$}C$_6$H$_5$)$_3$, 6 (pink triangle, $k_{obs}$=1.667±0.053 h$^{-1}$); rac-lactide and S-$\eta^5$-Pn*(H)Zr(O—CH{CH$_3$}C$_6$H$_5$)$_3$, 5 (blue triangle, $k_{obs}$=1.342±0.055 h$^{-1}$). Polymerisation conditions:chloroform-$d_1$ at 80° C. with $[LA]_0/[M]_0$=50, $[LA]_0$=0.5 M.

Figure 3:
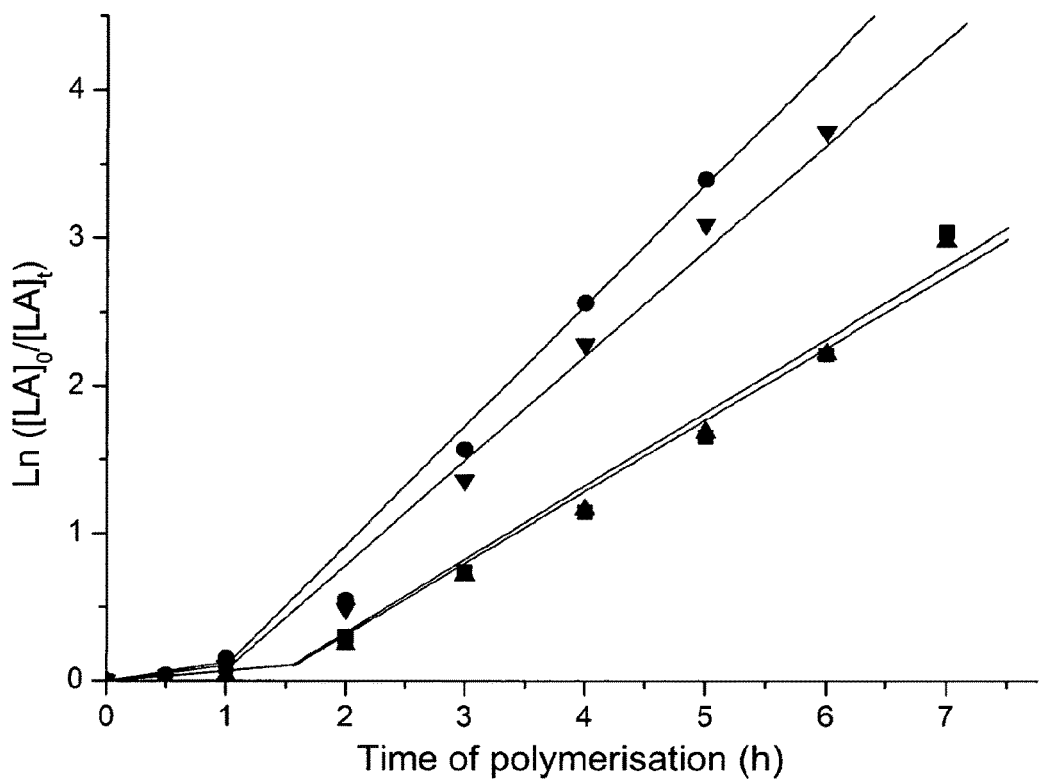

FIG. 3: Lactide polymerisation: L-lactide and S-$\eta^5$-Pn*(H)Zr(O—CH{CH$_3$}C$_6$H$_5$)$_3$, 5 (black square, $k_{obs}$=0.484±0.037 h$^{-1}$); L-lactide and rac-$\eta^5$-Pn*(H)Zr(O—CH{CH$_3$}C$_6$H$_5$)$_3$, 6 (red circle, $k_{obs}$=0.850±0.063 h$^{-1}$); rac-lactide and rac-$\eta^5$-Pn*(H)Zr(O—CH{CH$_3$}C$_6$H$_5$)$_3$, 6 (pink triangle, $k_{obs}$=0.767±0.037 h$^{-1}$); rac-lactide and S-$\eta^5$-Pn*(H)Zr(O—CH{CH$_3$}C$_6$H$_5$)$_3$, 5 (blue triangle, $k_{obs}$=0.491±0.031 h$^{-1}$). Polymerisation conditions:chloroform-$d_1$ at 60° C. with $[LA]_0/[M]_0$=50, $[LA]_0$=0.5 M.

Figure 4:
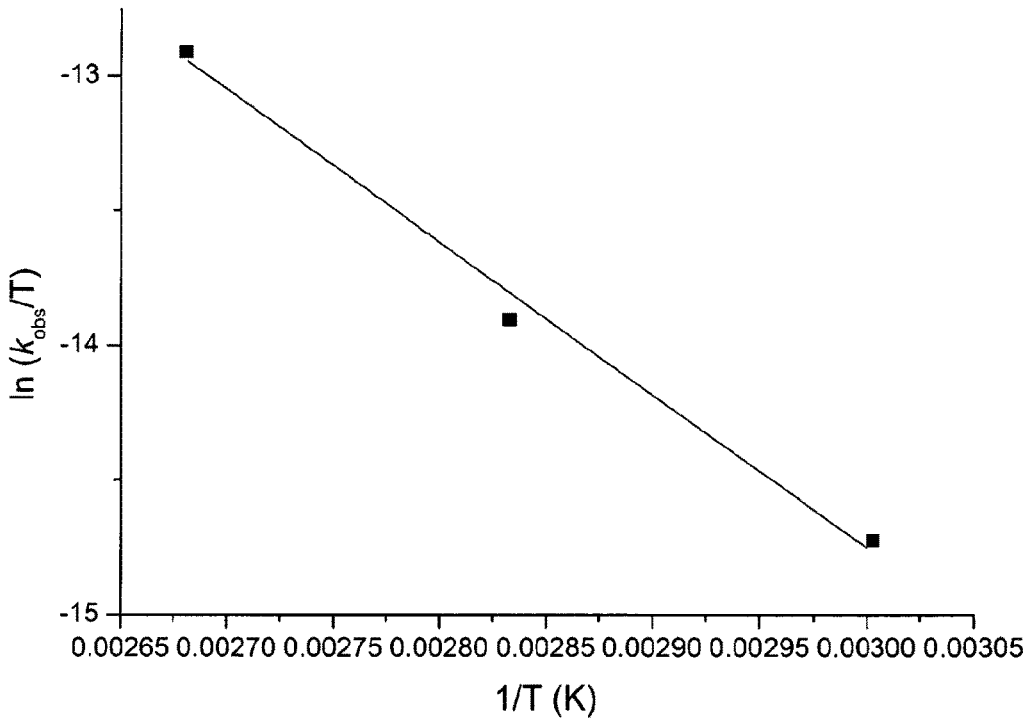

FIG. 4: Eyring plot of L-lactide polymerisation using S-$\eta^5$-Pn*(H)Zr(O—CH{CH$_3$}C$_6$H$_5$)$_3$, 5. Slope=-5610±488 with $R^2$=0.993. Polymerisation conditions: chloroform-$d_1$ with $[LA]_0/[Zr]_0$=50 and $[LA]_0$=0.5 M.

Figure 5:
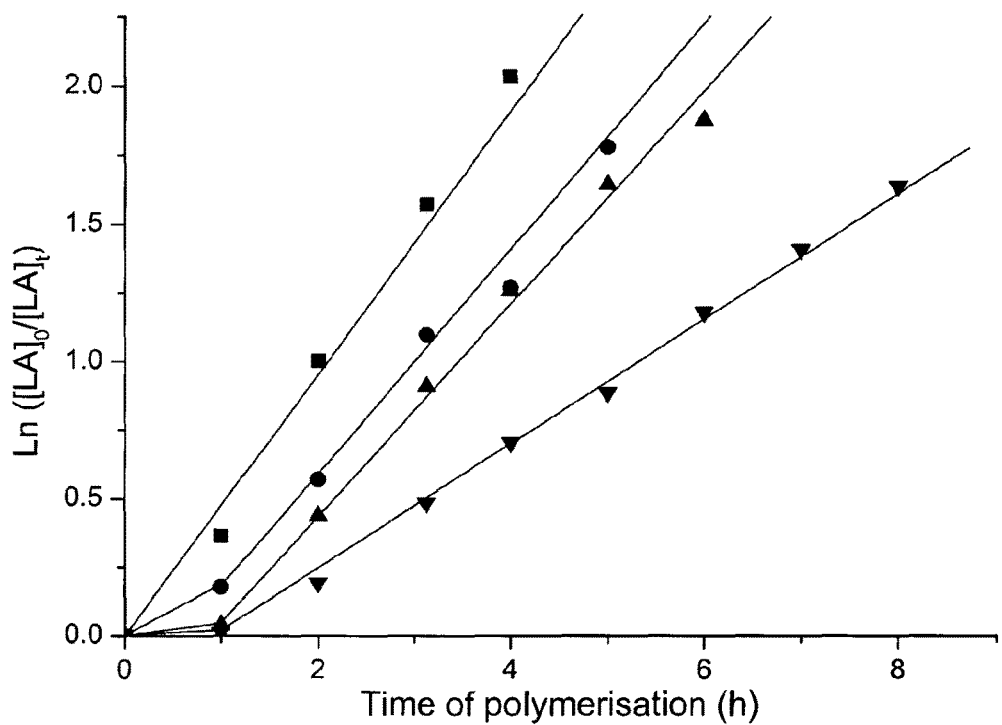

FIG. 5: L-lactide polymerisation using $\eta^5$-Pn*(H)Zr(O-2,6-$^i$Pr$_2$C$_6$H$_3$)$_3$, 8: $[LA]_0/[Zr]_0$=25 (black square, $k_{obs}$=0.521±0.021 h$^{-1}$); $[LA]_0/[Zr]_0$=50 (red circle, $k_{obs}$=0.391±0.022 h$^{-1}$); $[LA]_0/[Zr]_0$=100 (blue triangle, $k_{obs}$=0.377±0.015 h$^{-1}$); $[LA]_0/[Zr]_0$=200 (pink triangle, $k_{obs}$=0.235±0.004 h$^{-1}$). Polymerisation conditions:chloroform-$d_1$ at 100° C. with $[LA]_0$=0.5 M.

Figure 6:
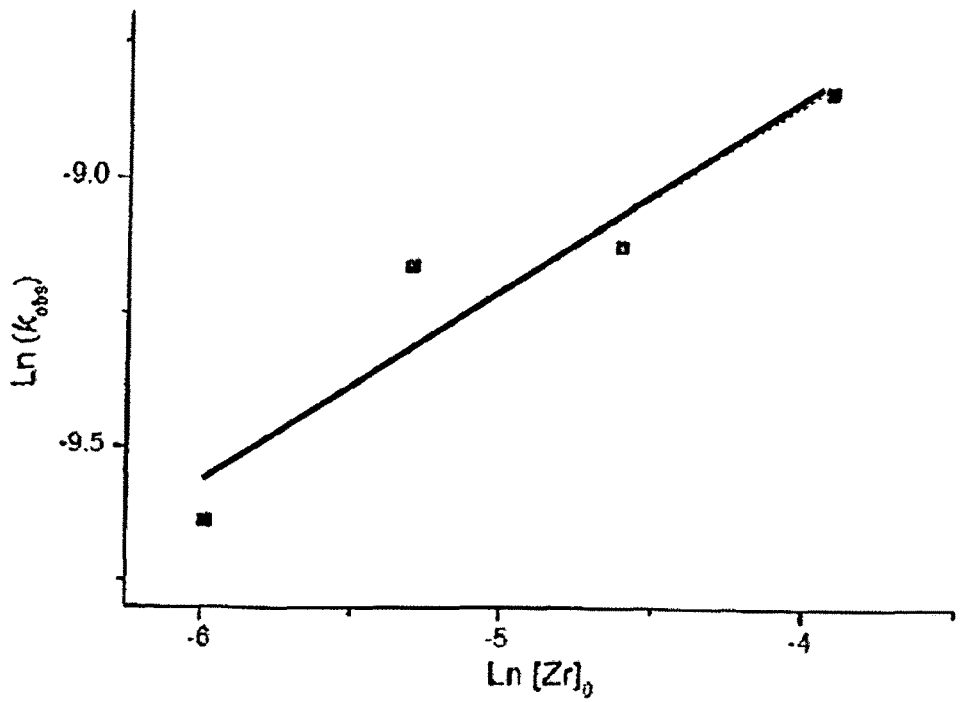

FIG. 6: Plot of Ln($k_{obs}$) vs Ln($[Zr]_0$) using $\eta^5$-Pn*(H)Zr(O-2,6-$^i$Pr$_2$C$_6$H$_3$)$_3$, 8. Slope=0.350±82 with $R^2$=0.901. Polymerisation conditions: chloroform-d at 100° C. and $[LA]_0$=0.5 M.

Figure 7:
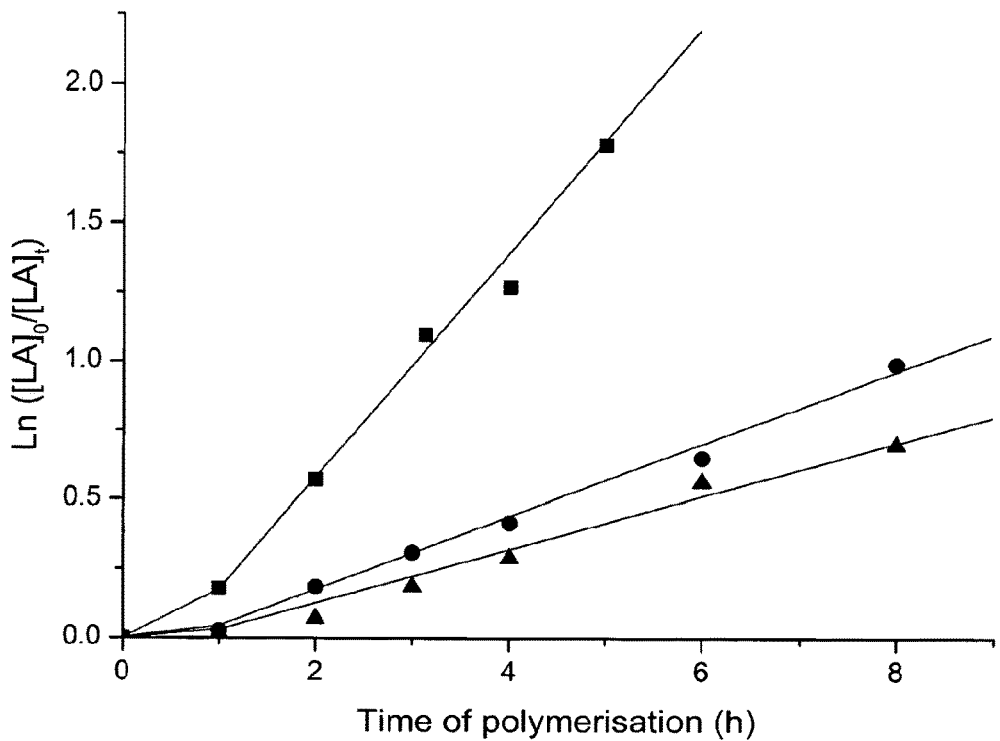

FIG. 7: L-lactide polymerisation using $\eta^5$-Pn*(H)Zr(O-2,6-$^i$Pr$_2$C$_6$H$_3$)$_3$, 8: T=100° C. (black square, $k_{obs}$=0.391±0.022 h$^{-1}$); T=90° C. (red circle, $k_{obs}$=0.151±0.008 h$^{-1}$); T=80° C. (blue triangle, $k_{obs}$=0.092±0.006 h$^{-1}$). Polymerisation conditions: chloroform-$d_1$ with $[LA]_0/[M]_0$=50, $[LA]_0$=0.5 M.

Figure 8:
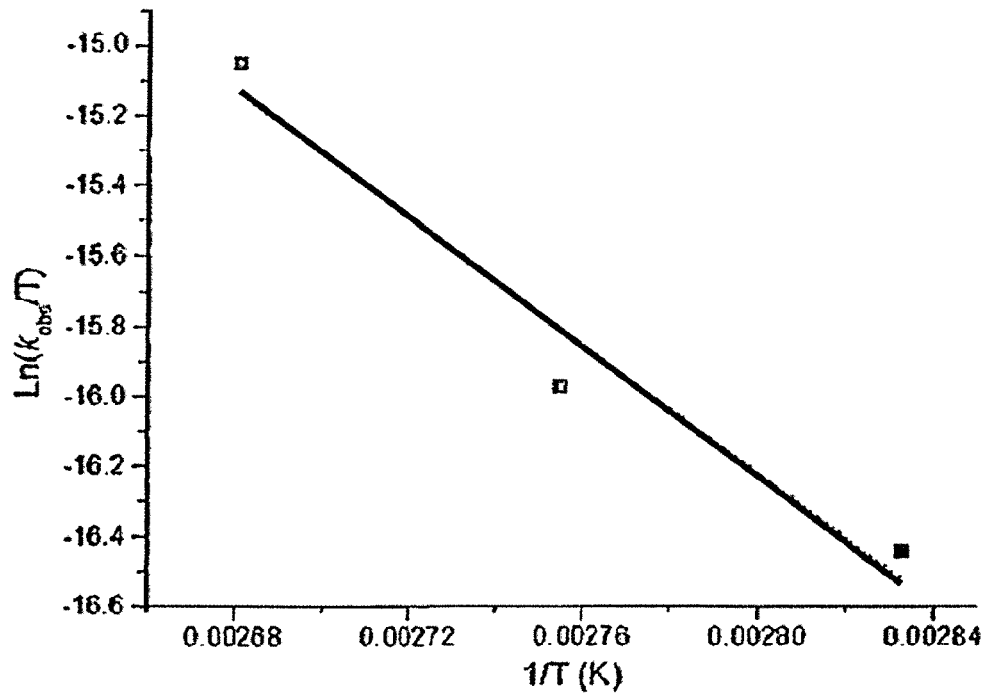

FIG. 8: Eyring plot of L-lactide polymerisation using $\eta^5$-Pn*(H)Zr(O-2,6-$^i$Pr$_2$C$_6$H$_3$)$_3$, 8. Slope=-9133±1881 with $R^2$=0.959. Polymerisation conditions: chloroform-$d_1$ with $[LA]_0/[Zr]_0$=50 and $[LA]_0$=0.5 M.

Figure 9:
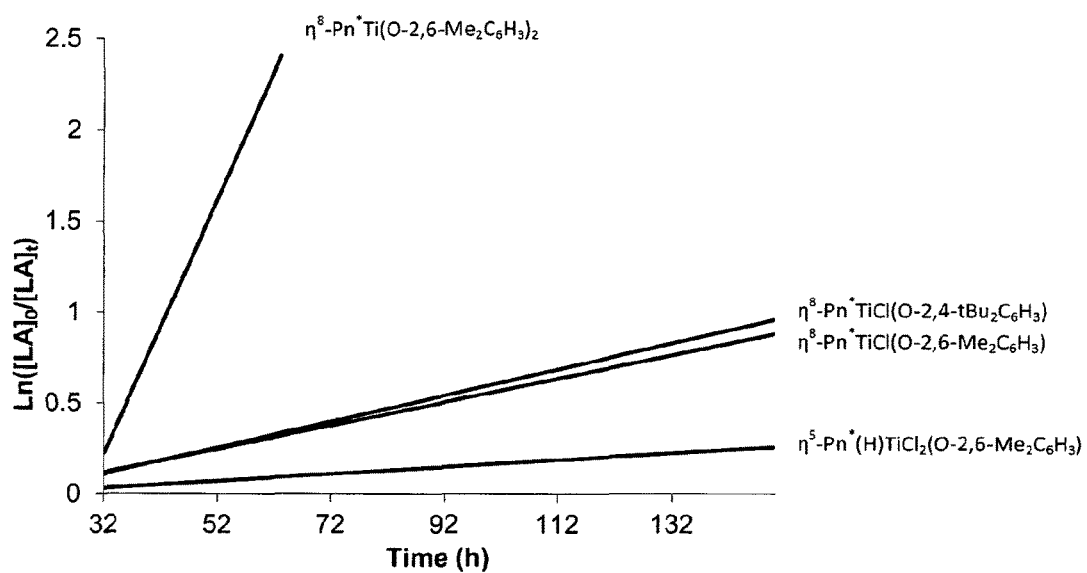

FIG. 9: Semi-logarithmic plots of L-lactide conversion us time, $[LA]_0/[Init]_0$=50, $[LA]_0$=0.104 M, T=80° C., benzene-$d_6$ (0.5 mL), using [$\eta^8$-(Pn*)Ti(O-2,6-Me$_2$C$_6$H$_3$)Cl], (green dotted line), [$\eta^8$-(Pn*)Ti(O-2,4-$^t$Bu$_2$C$_6$H$_3$)Cl], (black dashed line), [$\eta^8$-(Pn*)Ti(O-2,-6-Me$_2$C$_6$H$_3$)$_2$], (red line) and [$\eta^5$-(Pn*H)Ti(O-2,6-Me$_2$C$_6$H$_3$)Cl$_2$] (blue dot-dashed line). Induction period omitted.

Figure 10:
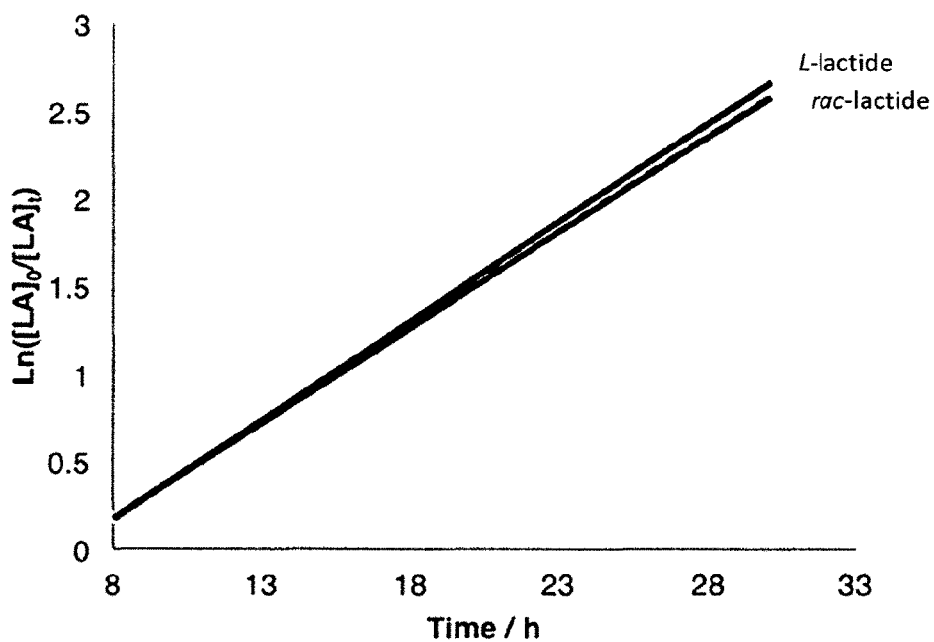

FIG. 10: Semi-logarithmic plots of lactide monomers conversion us time. Induction period omitted. $[LA]_0$=0.104 M, $[LA]_0/[init.]_0$=50, T=90° C., benzene-$d_6$. Polymerization using [$\eta^8$-(Pn*)Ti(O-2,6-Me$_2$C$_6$H$_3$)$_2$], L-lactide (red line) and rac-lactide (black dashed line).

Figure 11:
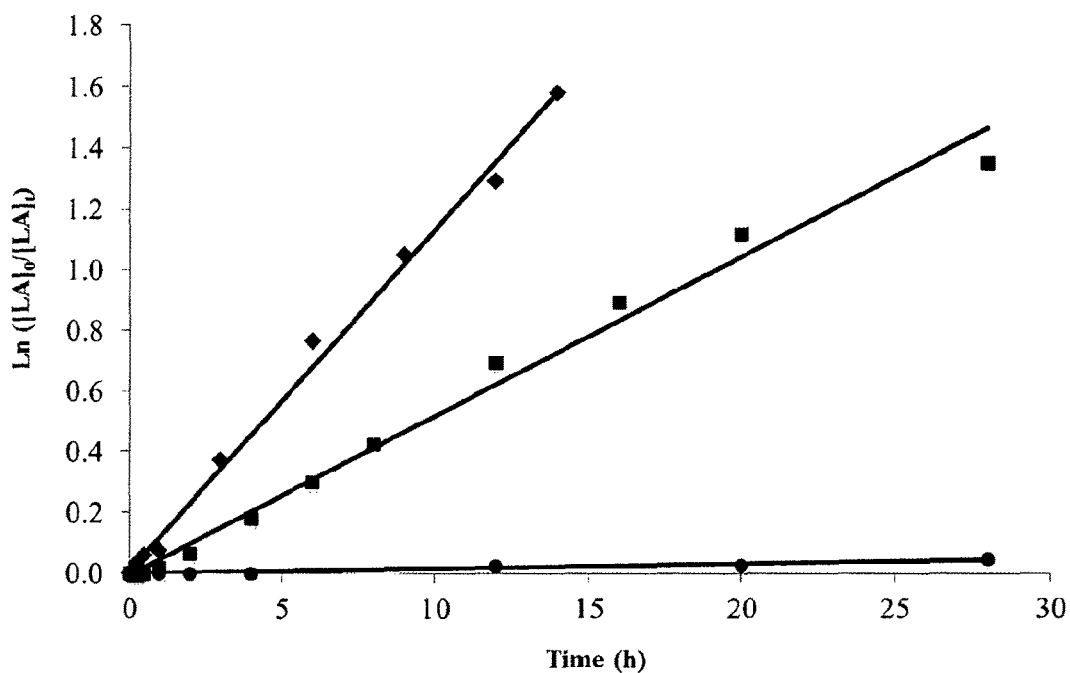

FIG. 11: Semi-logarithmic plots of L-lactide conversion vs time, $[LA]_0[Init]_0=50$, $[LA]_0=0.50$ M, T=80° C., chloroform-$d_1$ (0.5 mL), polymerisation using [(EBI)Zr(OC$_6$H$_3$Me$_2$-2,6)Cl], 1 (dotted line), [(Ind)$_2$Zr(O$^t$Bu)Me], 2 (solid line), [(Ind)$_2$Zr(OC$_6$H$_3$Me$_2$-2,6)Me], 3 (dashed line).

Figure 12:
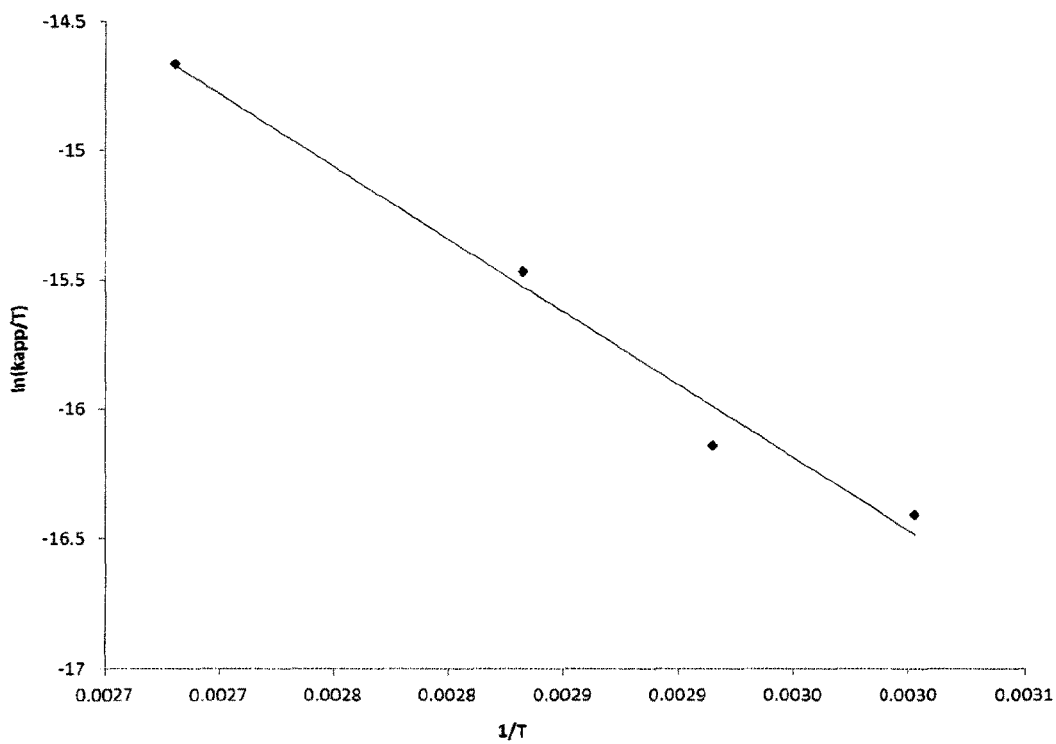

FIG. 12: Semi-logarithmic plots of the rate of propagation vs. the inverse of the temperature, $[LA]_0/[2]_0=50$, $[LA]_0=0.50$M, chloroform-$d_1$, $\Delta H^{\ddagger}=46.9$ kJ·mol$^{-1}$ and $\Delta S^{\ddagger}=-193.9$ J·K$^{-1}$·mol$^{-1}$.

Figure 13:
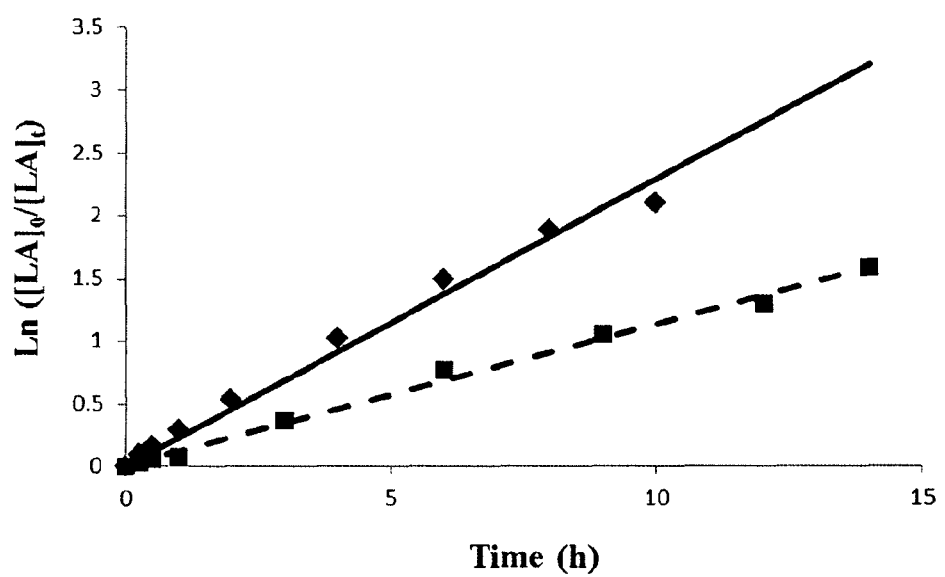

FIG. 13: Semi-logarithmic plots of lactide conversion vs time, $[LA]_0/[2]_0=50$, $[LA]_0=0.50$ M, T=80° C., chloroform-$d_1$ (0.5 mL); L-lactide (solid line), rac-lactide (dashed line).

EXAMPLE 1

Synthesis of [(Pn*)Ti(O-2,6-Me-C$_6$Me$_2$)Cl]

[$\eta^8$-(Pn*)TiCl($\mu$-Cl)]$_2$ (150 mg, 0.26 mmol) and [K(O-2,6-MeC$_6$H$_3$)] (78 mg, 0.50 mmol) were combined in toluene (30 mL) and left to stir for 25 h at room temperature. The resultant solution was filtered before being concentrated in vacuo. X-ray quality single crystals were obtained on storing the toluene concentrated solution at −35° C. for 24 h. Yield=52%. $^1$H NMR (benzene-d$_6$, 25° C., 300 MHz): δ 7.04 (d, 2H, $^3J_{HH}$=7.3 Hz, Ar—H), 6.82 (t, 1H, $^3J_{HH}$=7.4 Hz, Ar—H), 2.11, 2.06, 1.68 (s, 6H each, Pn-CH$_3$), 1.61 (s, 6H, Ar—CH$_3$). $^{13}$C{$^1$H} NMR (toluene-d$_8$, 25° C., 75.1 MHz): δ 130.69, 126.16, 14.36, 123.41, 120.41 (Quaternary carbons), 180.9 (Ar—CH$_3$) 13.20, 12.47, 11.11 (Pn-CH$_3$). The quaternary bridgehead carbon atoms were not observable and certain quaternary carbon signals were obscured by solvent resonances. Analysis calculated for C$_{22}$H$_{27}$ClTiO (%): C, 67.62; H, 6.98. found: C, 67.70; H, 7.03.

EXAMPLE 2

Synthesis of [$\eta^8$-(Pn*)Ti(O-2,4-$^t$Bu-C$_6$H$_3$)Cl]

[$\eta^8$-(Pn*)TiCl($\mu$-Cl)]$_2$ (150 mg, 0.25 mmol) and [K(O-2,4-$^t$Bu-C$_6$H$_3$)] (120 mg, 0.50 mmol) were stirred in toluene (30 mL) at room temperature for 48 h. The resultant solution was filtered and the solvent removed in vacuo. Subsequent dissolution in minimal hot benzene and storing at room temperature for 24 h led to the formation of X-ray quality single crystals. Yield=55%. $^1$H NMR (benzene-d$_6$, 25° C., 300 MHz): δ 7.54 (d, 1H, $^4J_{HH}$=2.4 Hz, meta-Ar—H), 7.18 (dd, 1H, $^3J_{HH}$=8.1 Hz, $^4J_{HH}$=2.4 Hz, meta-Ar—H), 6.41 (d, 1H, $^3J_{HH}$=8.3 Hz, ortho-Ar—H), 2.07, 1.80, 1.64 (s, 6H each, Pn-CH$_3$), 1.59 (s, 9H, C(CH$_3$)), 1.35 (s, 9H, C(CH$_3$)). $^{13}$C{$^1$H} NMR (benzene-d$_6$, 25° C., 75.1 MHz): δ 161.21 (ipso-Ar), 142.66, 140.76, 139.1, 0 135.5, 7 130.28, 124.62 (quaternary carbons), 123.82, 123.77 (meta-Ar) 122.82 (quaternary carbon) 121.22 (ortho-Ar), 35.55, 34.55 (Ar-CM$_3$), 31.95, 30.88 (Ar—CH$_3$), 13.04, 12.48, 10.84 (Pn-CH$_3$). Analysis calculated for C$_{28}$H$_{39}$TiClO (%): C, 70.8; H, 8.29. found: C, 70.65; H, 8.23.

EXAMPLE 3

Synthesis of [$\eta^8$-(Pn*)Ti(O-2,6-Me-C$_6$H$_3$)$_2$]

[$\eta^8$-Pn*TiCl($\mu$-Cl)]$_2$ (150 mg, 0.25 mmol) and [K(O-2,6-Me-C$_6$H$_3$)] (160 mg, 0.50 mmol) were stirred in toluene (30 mL) for 24 h at 25° C. The resultant solution was filtered and subsequently concentrated in vacuo. X-ray quality single crystals were obtained on storing the toluene concentrated solution at −35° C. for 24 h. Yield=62%. $^1$H NMR (benzene-d$_6$, 25° C., 300 MHz): δ 6.96 (d, 4H, $^3J_{HH}$=7.5 Hz, meta-Ar—H), 6.69 (t, 2H, $^3J_{HH}$=7.3 Hz, para-Ar—H), 2.13 (s, 12H, Pn-CH$_3$), 1.81 (s, 12H, Ar—CH$_3$), 1.77 (s, 6H, Pn-CH$_3$). $^{13}$C{$^1$H} NMR (benzene-d$_6$, 25° C., 75.1 MHz): δ 162.52 (ipso-Ar), 139.73 130.97 125.22 120.47 118.89 (quaternary carbons), 17.73 (Ar—CH$_3$), 11.90 10.89 (Pn-CH$_3$). The quaternary bridgehead carbon atoms were not observable. Analysis calculated for C$_{30}$H$_{36}$TiO$_2$(%): C, 75.62; H, 7.63. Found: C, 75.48; H, 7.77.

EXAMPLE 4

Synthesis of [$\eta^8$-(Pn*)Ti(O$^t$Bu)Cl]

[$\eta^8$-(Pn*)TiCl($\mu$-Cl)]$_2$ (150 mg, 0.25 mmol) and [K(O$^t$Bu)] (53 mg, 0.50 mmol) were combined in toluene (30 mL) and left to stir for 2 h at room temperature. The resultant solution was filtered and the solvent was removed under reduced pressure. Minimal hot hexane was added and X-ray quality single crystals were obtained on cooling to room temperature and storing at −35° C. for 24 h. Yield=54%. $^1$H NMR (benzene-d$_6$, 25° C., 300 MHz): δ 2.09, 1.90, 1.62 (s, 6H each, Pn-CH$_3$), 1.31 (s, 9H, C(CH$_3$)). $^{13}$C{$^1$H} NMR (benzene-d$_6$, 25° C., 75.1 MHz): δ 138.41, 136.38 (Pn-bridgehead), 128.86, 122.16, 121.91 (Pn), 81.16 (C(CH$_3$)), 32.48 (C(CH$_3$)), 13.09, 12.85, 10.86 (Pn-CH3).

EXAMPLE 5

Synthesis of [$\eta^8$-(Pn*)Ti(O$^t$Bu)$_2$]

[$\eta^8$-(Pn*)TiCl($\mu$-Cl)]$_2$ (20 mg, 0.035 mmol) and [K(O$^t$Bu)] (16 mg, 0.14 mmol) were combined in benzene-d$_6$ (1 mL). The resulting dark red solution was filtered and allowed to undergo a slow evaporation, which led to the formation of X-ray quality single crystals. $^1$H NMR (benzene-d$_6$, 25° C., 300 MHz): δ 2.08 (s, 12H, Pn-CH$_3$), 1.76 (s, 6H, Pn-CH3), 1.31 (s, 18H, C(CH$_3$)). $^{13}$C{$^1$H} NMR (benzene-d$_6$, 25° C., 75.1 MHz): 134.38, 128.71, 116.58 (Pn) 76.44 (C(CH$_3$)) 33.60 (C(CH$_3$)) 13.07, 10.81 (Pn-CH$_3$). The quaternary bridgehead carbon atoms were not observable.

EXAMPLE 6

Synthesis of [$\eta^5$-(Pn*H)Ti(O-2,6-Me-C$_6$H$_3$)C)$_2$]

[$\eta^5$-Pn*TiCl($\mu$-Cl)]$_2$ (350 mg, 0.57 mmol) and [H(O-2,6-Me-C$_6$H$_3$)] (139 mg, 1.14 mmol) were stirred in toluene (50 mL) at 85° C. for 24 h, before being filtered and concentrated under vacuum. X-ray quality single crystals were formed on storing the concentrated solution at −35° C. for 24 h. Yield=68%. $^1$H NMR (benzene-d$_6$, 25° C., 300 MHz): δ 6.82-6.72 (m, 3H, Ar—H), 3.19 (q, 1H, $^3J_{HH}$=7.3 Hz, Pn-H), 2.24 (s, 6H, Ar—CH$_3$), 2.23, 2.12, 2.08, 1.79, 1.44 (s, 3H each, Pn-CH$_3$), 0.84 (d, 3H, $^3J_{HH}$=7.5 Hz, Pn-CH$_3$). $^{13}$C{$^1$H} NMR (benzene-d$_6$, 25° C., 75.1 MHz) δ 162.73 (ipso-Ar), 150.62, 147.79, 141.18, 136.86, 129.80, 129.07 (Quaternary Carbons), 128.13 (meta-Ar) 123.70 (Quaternary Carbons) 123.06 (para-Ar), 44.19 (sp$^3$ Pn), 17.22 (Ar—CH$_3$), 15.53, 14.08, 13.53, 13.23, 11.75, 11.59 (Pn-CH3). The quaternary bridgehead carbon atoms were not observable. Analysis calculated for C$_{22}$H$_{28}$Cl$_2$TiO (%): C, 61.84; H, 6.62. Found: C, 61.71; H, 6.70.

EXAMPLE 7

Synthesis of [η$^5$-(Pn*H)Ti(O-2,6-Me-C$_6$H$_3$)$_3$]

A solution of [η$^5$-(Pn*H)Ti(OC$_6$H$_3$Me$_2$-2,6)Cl$_2$] (50 mg, 0.12 mmol) and [K(O-2,6-Me$_2$C$_6$H$_3$)](37.5 mg, 0.24 mmol) in toluene (10 mL) was stirred for 30 minutes at 100° C. The resultant bright orange solution was filtered and the solvent removed under reduced pressure. Subsequent dissolution in minimal hot hexane followed by storage at −35° C. for 24 h led to the formation of X-ray quality single crystals. Yield=65%. $^1$H NMR (benzene-d$_6$, 25° C., 300 MHz): δ 6.90 (d, 6H, $^3J_{HH}$=7.2 Hz, meta-Ar—H), 6.73 (t, 3H, $^3J_{HH}$=7.3 Hz, para-Ar—H) 3.59 (q, 1H, $^3J_{HH}$=7.7 Hz, Pn-H) 2.28 (s, 18H, Ar—CH$_3$) 2.21, 2.14, 1.96, 1.58, 1.53 (s, 3H each, Pn-CH$_3$) 1.08 (d, 3H, $^3J_{HH}$=7.32 Hz, Pn-CH$_3$). $^{13}$C{$^1$H} NMR (benzene-d$_6$, 25° C., 75.1 MHz) δ 164.05 (ipso-Ar), 147.30, 144.11, 138.88, 130.71 (Pn), 129.06 (Ar), 128.93 (Pn), 127.41 (Ar), 122.49 (Pn), 120.79 (Ar), 116.96 (Pn), 44.46 (sp$^3$ Pn), 18.15 (sp$^3$ Pn-CH$_3$), 15.33, 13.37, 12.49, 11.99, 11.75, 11.58 (Pn-CH$_3$).

Crystallographic Details

η$^8$-(Pn*)Ti(O-2,6-Me-C$_6$H$_3$)Cl

Single crystals were grown from a toluene solution at −35° C., C$_{22}$H$_{27}$ClOTi, M$_r$=390.81, triclinic, P-1, a=11.2997(2) Å, b=11.6154(2) Å, c=15.7437(3) Å, α=77.0104(7)°, β=89.3195(7)°, γ=85.2957(8)°, V=2006.66(6)Å$^3$, Z=4, T=150 K, prism, red brown, 9129 independent reflections, R(int)=0.038, R$_1$=0.046 wR$_2$=0.133 [I>2σ(I)].

η$^8$-(Pn*)Ti(O-2,4-$^t$Bu-C$_6$H$_3$)Cl

Single crystals were grown from a benzene solution at −35° C., C$_{28}$H$_{39}$ClOTi, M$_r$=474.97, monoclinic, P$_{21}$/n, a=11.7910(1) Å, b=9.5199(1) Å, c=23.5743(3) Å, α=102.4652(5)°, β=90° γ=90°, V=2583.82(5) Å$^3$, Z=4, T=150 K, block, purple, 5884 independent reflections, R(int)=0.029, R$_1$=0.038 wR$_2$=0.091 [I>2σ(I)].

η$^8$-(Pn*)Ti(O-2,6-Me-C$_6$H$_3$)$_2$

Single crystals were grown from a toluene solution at −35° C., C$_{30}$H$_{36}$O$_2$Ti, M$_r$=476.51, Orthorhombic, Pbca, a=9.2631(1) Å, b=15.4563(1) Å, c=35.7542(3) Å, α=90°, β=90° γ=90°, V=5.119.32(8)Å$^3$, Z=8, T=150 K, block, dark red, 5807 independent reflections, R(int)=0.036, R$_1$=0.047 wR$_2$=0.092 [I>2σ(I)].

η$^8$-(Pn*)Ti(O$^t$Bu)Cl

Single crystals were grown from a hexane solution at −35° C., C$_{18}$H$_{27}$ClOTi, M$_r$=342.76, triclinic, P-1, a=8.8527(1)Å, b=10.1475(2)Å, c=10.7183(2)Å, α=79.8812(7)°, β=78.4070(7)°, γ=73.9368(7)°, V=898.98(3)Å$^3$, Z=2, T-150 K, block, dark red, 4073 independent reflections, R(int)=0.016, R$_1$=0.034 wR$_2$=0.085 [I>2σ(I)].

η$^8$-(Pn*)Ti(O$^t$Bu)$_2$

Single crystals were grown from a benzene solution at −35° C., C$_{22}$H$_{36}$O$_2$Ti, M$_r$=380.43, monoclinic, P2$_1$/n, a=12.7185(2)Å, b=10.9762(1)Å, c=15.9690(2)Å, α=90°, β=93.2853(6)°, γ=90°, V=2225.62(5)Å$^3$, Z=4, T=150 K, prism, red brown, 5062 independent reflections, R(int)=0.022, R, =0.075 wR$_2$=0.188 [I>2σ(I)].

η$^5$-(Pn*H)Ti(O-2,6-Me-C$_6$H$_3$)Cl$_2$

Single crystals were grown from hexane solution at −35° C., C$_{22}$H$_{28}$Cl$_2$TiO, M=427.27, monoclinic, P21/c, a=8.5552(2)Å, b=17.7148(5)Å, c=14.6706(4)Å, α=γ=90.000, β=106.6445(11), V=2130.22(10)Å$^3$, T=150(2) K, Z=4, 4844 independent reflections, R(int)=0.019 R$_1$=0.054 wR$_2$=0.119 [I>2σ(I)].

η$^5$-(Pn*H)Ti(O-2,6-Me-C$_6$H$_3$)$_3$

Single crystals were grown from hexane solution at −35° C., C$_{38}$H$_4$TiO$_3$, M=598.68, monoclinic, P21/n, a=8.9702(2) Å, b=24.3863(6)Å, c=14.6936(4)Å, α=γ=90.000, β=91.352(2), V=3213(14)Å$^3$, T=150(2) K, Z=4, 6634 independent reflections, R(int)=0.060 R$_1$=0.056 wR$_2$=0.141 [I>2σ(I)].

Experimental Detail II—Relating to (Hydro)Permethylentalenes

General Procedure

All organometallic syntheses were performed under an inert atmosphere of nitrogen gas, utilizing standard Schlenk techniques on a dual vacuum-inlet gas manifold or Braun glove box. Where necessary, solvents were dried by reflux over the appropriate drying agent: NaK (Et$_2$O), sodium (THF) and SPS drying system (hexane, pentane, soluene). Solvents were distilled from the desiccant under a flowing stream of nitrogen and transferred using a siphoning technique via steel cannulae and stored in flame-dried glass ampoules under an atmosphere of nitrogen. Deuterated NMR solvents were dried over NaK (benzene-d$_6$, toluene-d$_8$) or CaH$_2$ (pyridine-d$_5$), vacuum transferred and freeze-pump-thaw-degassed three times prior to use. Elemental analyses were conducted by Mr Stephen Boyer at the elemental analysis service at London Metropolitan University. NMR spectra were recorded using Young's tap NMR tubes on a Varian Mercury VX-Works 300 MHz spectrometer. $^1$H and $^{13}$C{$^1$H} NMR spectra were referenced to the residual protio-solvent peak.

X-Ray Crystallography

Crystals were mounted on glass fibres using perfluoropolyether oil, transferred to a goniometer head on the diffractometer and cooled rapidly to 150 K in a stream of cold nitrogen using an Oxford Cryosystems CRYOSTREAM unit. Data collections were performed using an Enraf-Nonius FR590 KappaCCD diffractometer, utilising graphite-monochromated Mo K$_α$ X-ray radiation (λ=0.71073 Å). Intensity data were processed using the DENZO-SMN package. Structures were solved using the direct-methods program SIR92, and refined using full-matrix least squares refinement on all F2 data using the CRYSTALS program suite.

Polymerisation Procedure

The lactide monomer (40 mg) and the complex were introduced in an NMR tube following the desired monomer: initiator ratio. Then 0.57 mL of chloroform-d$_1$ was added to the compounds, leading to an initial monomer concentration of [LA]$_0$=0.5 M. The solution was monitored by $^1$H NMR spectroscopy. The conversion was determined by integration of the methane area of the polymer versus the monomer.

EXAMPLE 8

Synthesis of Pn*(H)SnMe$_3$

To a slurry of Pn*(H)Li (20.9 g, 10.7 mmol) in pentane (20 mL) at −78° C. was added a solution of SnMe$_3$Cl (2.14 g, 10.7 mmol) in pentane (10 mL). The reaction mixture was warmed to room temperature and stirred for 3 h to afford an orange solution and colourless precipitate of LiCl. This was filtered and the volatiles were removed in vacuo to afford Pn*(H)SnMe$_3$ (50:50 mixture of diastereomers judged by $^1$H NMR spectroscopy) as an orange oil. Yield: 3.56 g (97%). $^1$H NMR (benzene-d$_6$, 23° C.): δ 2.98 (q, 1H, $^3J_{HH}$=7.2 Hz, Pn*(H)), 20.9 2.05 2.00 (s, 3H each, CH$_3$-Pn*(H)), 1.95 (overlapping s, 3H each, CH$_3$-Pn*(H)) 1.93 1.83 (s, 3H each, CH$_3$-Pn*(H)), 1.70 (overlapping s, 3H each, CH$_3$-Pn*(H)), 1.59 (s, 3H, CH$_3$-Pn*(H)), 1.18 (d, 3H $^3J_{HH}$=7.2 Hz, 1-CH$_3$-Pn*(H)), 0.94 (d, 3H, $^3J_{HH}$=6.9 HZ, 1-CH$_3$-Pn*(H)), −0.01 (s, 9H, $^2J_{1H-119Sn}$=25.2 Hz, $^2J_{1H-117Sn}$=24.2 Hz, 5-SnMe$_3$-Pn*(H))—0.03 (s, 9H, $^2J_{1H-119Sn}$=25.3 Hz, $^2J_{1H-117Sn}$=24.3 Hz, 5-SnMe$_3$-Pn*(H)). $^{13}$C{$^1$H} NMR (benzene-d$_6$, 23° C.): 150.2 147.2 144.6 144.4 129.8 129.4 121.3 119.6 (6×overlapping resonances, (q-Pn*(H)), 44.3 41.8 (1-Pn*(H)), 13.5 13.4 12.8 12.4 121.3 12.2 12.1 12.0 (2×overlapping resonances CH$_3$-Pn*(H)), 18.2 17.6 (1-CH$_3$-Pn*(H)), −8.8 (5-SnMe$_3$-Pn*(H), $^2J_{1H-119Sn}$=153 Hz, $^2J_{1H-117Sn}$=148 Hz), −9.2 (5-SnMe$_3$-Pn*(H), $^2J_{1H-119Sn}$=157 Hz, $^2J_{1H-117Sn}$=150 Hz).

EXAMPLE 9

Synthesis of Pn*(H)TiCl$_3$

To a slurry of TiCl$_4$(thf)$_2$ (0.408 g, 1.44 mmol) in benzene (2 mL) was added a solution of Pn*(H)SnMe$_3$ (0.505 g, 1.44 mmol) in benzene (2 mL) to afford a dark-purple solution. The reaction mixture was heated to 80° C. for 4 hr. The volatiles were removed in vacuo to afford Pn*(H)TiCl$_3$, as a purple powder. Yield: 0.363 g (74%). Single crystals suitable for an X-ray diffraction study were grown from saturated Et$_2$O solution at −35° C. $^1$H NMR (benzene-d$_6$, 23° C.): δ 0.85 (d, 3H, $^3J_{HH}$=7.5 Hz, 1-CH$_3$-Pn*(H)), 1.57 1.89 2.02 2.03 2.14 (s, 3H each, CH$_3$-Pn*(H)), 3.80 (q, 1H, $^3J_{HH}$=8.5 Hz, Pn*(H)). $^{13}$C{$^1$H} NMR (benzene-d$_6$, 23° C.): δ 153.6 152.7 147.4 140.6 133.3 131.3 127.4 (q-Pn*(H)), 46.8 (1-Pn*(H)), 15.4 (1-CH$_3$-Pn*(H)), 14.5, 14.4, 14.2, 12.2, 11.6 (CH$_3$-Pn*(H)).

EXAMPLE 10

Synthesis of [Pn*(H)ZrCl$_3$]2

To a slurry of ZrCl$_4$ (0.995 g, 4.27 mmol) in benzene (5 mL) was added a solution of Pn*(H)SnMe$_3$ (1.50 g, 4.27 mmol) in benzene (5 mL). The reaction mixture was heated to 80° C. for 72 h to afford a dark-green solution. The volatiles were removed in vacuo to yield a green solid. To this was added pentane (15 mL) and the reaction mixture was sonicated for 15 minutes to afford a fine, olive-green powder and a pale-yellow solution. The reaction mixture was filtered and the filtrate was dried under reduced pressure to afford [Pn*(H)ZrCl$_3$]$_2$, as an olive-green powder. Yield: 1.42 g (87%). Single crystals were grown from a saturated benzene solution at 23° C. $^1$H NMR (benzene-d$_6$, 23° C.): δ 0.92 (d, 3H, $^3J_{HH}$=7.5 Hz, 1-CH$_3$-Pn*(H)), 1.81 2.01 2.06 2.17 2.19 (s, 3H each, CH$_3$-Pn*(H)), 3.50 (q, $^3J_{HH}$=7.5 Hz, Pn*(H)). $^{13}$C{$^1$H} NMR (benzene-d$_6$, 23° C.): δ 151.0 147.0 142.1 133.5 129.5 127.4 120.7 (q-Pn*(H), 46.0 (1-Pn*(H)), 15.6 (1-CH$_3$-Pn*(H)), 14.2 13.6 13.5 12.3 12.2 (CH$_3$-Pn*(H)).

EXAMPLE 11

Synthesis of [Pn*(H)HfCl$_3$]$_2$

To a slurry of HfCL$_4$ (0.164 g, 0.467 mmol) in benzene (2 mL) was added a solution of Pn*(H)SnMe$_3$ (0.149 g, 0.467 mmol) in benzene (2 mL). The reaction mixture was heated to 80° C. for 2 h to afford an orange solution. The volatiles were removed in vacuo to yield [Pn*(H)HfCL$_3$]$_2$, as a pale-yellow solid. Single crystals were grown from a saturated benzene solution at room temperature. $^1$H NMR (benzene-d$_6$, 23° C.): δ 0.93 (d, 3H, $^3J_{HH}$=7.4 Hz, 1-CH$_3$-Pn*(H)), 1.62 1.84 2.01 2.01 2.10 (s, 3H each, CH$_3$-Pn*(H)), 3.42 (q, $^3J_{HH}$=7.4 Hz, Pn*(H)). $^{13}$C{$^1$H} NMR (benzene-d$_6$, 23° C.): δ 150.0, 142.3, 137.2, 123.9, 117.4 (q-Pn*(H)), 45.5 (1-Pn*(H)), 15.9 (1-CH$_3$-Pn*(H)) 12.2 12.1 12.0 11.9 11.6 (CH$_3$-Pn*(H)).

EXAMPLE 12

Synthesis of η$^5$-Pn*(H)Ti(O$^t$Bu)$_3$

Pn*(H)TiCl$_3$ (0.020 g, 0.059 mmol) and KO$^t$Bu (0.020 g, 0.18 mmol) were combined in benzene-d$_6$ (0.5 mL) and sonicated for 5 minutes to afford a clear, pale-yellow solution and colourless precipitate. Filtration followed by drying of the filtrate in vacuo afforded Pn*(H)Ti(O$^t$Bu)$_3$, 1, as a pale-yellow powder. $^1$H NMR (benzene-d$_6$, 23° C.): δ 3.35 (q, $^3J_{HH}$=7.2 Hz, Pn*(H)), 2.27 2.24 2.12 2.08 1.84 (s, 3H each, CH$_3$. Pn*(H)), 1.30 (s, 27H, OC(CH$_3$)$_3$), 1.25 (d, 3H $^3J_{HH}$=7.3 Hz, 1-CH$_3$-Pn*(H)). $^{13}$C{$^1$H} NMR (benzene-d$_6$, 23° C.): δ 141.5 135.1 132.9 128.6 121.0 115.6 110.5 (q-Pn*(H)), 75.4 (OC(CH$_3$)$_3$), 43.7 (1-Pn*(H)), 33.4 (OC(CH$_3$)$_3$), 16.2 (1-CH$_3$-Pn*(H)), 12.7 12.6 12.1 12.1 11.4 (CH$_3$-Pn*(H)).

EXAMPLE 13

Synthesis of η$^5$-Pn*(H)Zr(O$^t$Bu)$_3$

[Pn*(H)ZrCl$_3$]$_2$(0.028 g, 0.036 mmol) and KO$^t$Bu (0.024 g, 0.22 mmol) were combined in benzene-d$_6$ (0.5 mL) and sonicated for 5 minutes to afford a clear pale-yellow solution and colourless precipitate. Filtration followed by drying of the filtrate in vacuo afforded Pn*(H)Zr(O$^t$Bu)$_3$ as a pale-yellow powder. $^1$H NMR (benzene-d$_6$, 23° C.): δ 3.33 (q, $^3J_{HH}$=6.9 Hz, Pn*(H)), 2.25 2.22 20.9 2.05 1.83 (s, 3H each, CH$_3$-Pn*(H)), 1.35 (s, 27H, OC(CH$_3$)$_3$), 1.23 (d, 3H, $^3J_{HH}$=6.9 Hz, 1-CH$_3$-Pn*(H)). $^{13}$C{$^1$H} NMR (benzene-d$_6$, 23° C.): δ 142.8 137.5 134.4 129.3 123.4 117.8 112.9 (q-Pn*(H)), 80.2 (OC(CH$_3$)$_3$), 43.8 (1-Pn*(H)), 33.1 (OC(CH$_3$)$_3$), 15.9 (1-CH$_3$-Pn*(H)), 13.7, 12.8, 12.7, 12.3 12.2 (CH$_3$-Pn*(H)).

EXAMPLE 14

Synthesis of η$^5$-Pn*(H)Zr(O—CH$_2$C$_6$H$_5$)$_3$

[Pn*(H)ZrCl$_3$]$_2$(0.100 g, 0.131 mmol) and KO—CH$_2$C$_6$H$_5$ (0.115 g, 0.786 mmol) were combined in C$_6$H$_6$ (5 mL) and stirred for 10 minutes to afford a clear, pale-yellow solution and colourless precipitate. Filtration followed by drying of the filtrate in vacuo afforded Pn*(H)

Zr(O—CH$_2$C$_6$H$_5$)$_3$ as a pale-yellow oily solid at room temperature. $^1$H NMR (benzene-d$_6$, 23° C.); δ 7.37-7.03 (overlapping m, 15H, CH$_2$C$_6$H$_5$), 5.10 (s, 6H, CH$_2$C$_6$H$_5$), 3.12 (q, 1H, $^3J_{HH}$=7.3 Hz, Pn*(H)), 2.13 20.9 1.99 1.90 1.68 (s, 3H each CH$_3$-Pn*(H)), 1.13 (d, 3H $^3J_{HH}$=7.3 Hz, 1-CH$_3$-Pn*(H)). $^{13}$C{$^1$H} NMR (benzene-d$_6$, 23° C.): δ 143.9 (CH$_2$-1-C$_6$H$_5$), 143.0 135.4 133.2 (q-Pn*(H)), 128.5 (CH$_2$-2,3,4-C$_6$H$_5$), 127.1 (q-Pn*(H)), 126.9 126.4 (CH$_2$-2,3,4-C$_6$H$_5$), 122.0 116.5 111.3 (q-Pn*(H)), 71.7 (CH$_2$C$_6$H$_5$), 43.2 (1-Pn*(H)), 16.2 (1-CH$_3$-Pn*(H)), 12.3 11.8 11.5 11.0 10.4 (CH$_3$-Pn*(H)).

EXAMPLE 15

Synthesis of η$^5$-Pn*(H)Zr(O—S—CH{CH$_3$}C$_6$H$_5$)$_3$

Pn*(H)ZrCl$_3$ and S—KOCH{CH$_3$}C$_6$H$_5$ were combined in benzene (5 mL) and stirred for 10 minutes to afford a clear, pale-yellow solution and colourless precipitate. Filtration followed by drying of the filtrate in vacuo afforded η$^5$-Pn*(H)Zr(O—S—CH{CH$_3$}C$_6$H$_5$)$_3$, as a pale-yellow oily solid at room temperature. $^1$H NMR (benzene-d$_6$, 23° C.): Two diastereomers: δ 7.40 (d, 6H, $^3J_{HH}$=7.3 Hz, 2,6-C$_6$H$_5$), 7.11 (m, 3H, 4-C$_6$H$_5$), 5.30 (q, 3H, $^3J_{HH}$=6.1 Hz, CHMe), 3.14 30.9 (q, $^3J_{HH}$=6.9 HZ, Pn*(H)), 2.11 2.11 2.08 2.05 1.97 1.97 1.89 1.88 1.70 1.65 (overlapping s, 3H each, CH$_3$-Pn*(H)), 1.44 (d, 9H, $^3J_{HH}$=6.1 Hz, CHMe), 1.12 (d, 3H, $^3J_{HH}$=6.9 Hz, 1-CH$_3$-Pn*(H)). $^{13}$C{$^1$H} NMR (benzene-d$_6$, 23° C.): Diastereomer 1: δ 148.7 142.7 135.5 133.3 (q-Pn*(H)), 128.6 (3,5-C$_6$H$_5$), 126.9 (2,6-C$_6$H$_5$), 125.7 (q-Pn*(H)), 125.7 (4-C$_6$H$_5$), 122.0 116.4 111.4 (q-Pn*(H)), 77.0 (CHMe), 43.4 (1-Pn*(H)), 28.4 (CHMe), 16.1 (1-CH$_3$-Pn*(H)), 12.2 11.8 11.3 11.2 10.6 (CH$_3$-Pn*(H)). Diastereomer 2: 148.7 142.7 135.3 133.2 (q-Pn*(H)), 128.5 (3,5-C$_6$H$_5$), 126.9 (2,6-C(H$_5$), 125.9 (4-C$_6$H$_5$), 125.5 (q-Pn*(H)), 121.8 116.4 111.1 (q-Pn*(H)), 77.0 (CHMe), 43.3 (1-Pn*(H)), 28.4 (CHMe), 16.1 (1-CH$_3$-Pn*(H)), 12.2 11.8 11.7 11.2 10.5 (CH$_3$-Pn*(H)).

EXAMPLE 16

Synthesis of η$^5$-Pn*(H)Zr(O-rac-{CH$_3$}C$_6$H$_5$)$_3$

Pn*(H)ZrCL$_3$ and rac-KOCH{CH$_3$}C$_6$H$_5$ were combined in benzene (5 mL) and stirred for 10 minutes to afford a clear, pale-yellow solution and colourless precipitate. Filtration followed by drying of the filtrate in vacuo afforded η$^5$-Pn*(H)Zr(O-rac-CH{CH$_3$}C$_6$H$_5$)$_3$, as a pale-yellow oily solid at room temperature. $^1$H NMR (benzene-d$_6$, 23° C.): Mixture of diastereomers: δ 7.48-7.10 (overlapping m, 15H, C$_6$H$_5$), 5.24 (overlapping q, 3H, CHMe), 3.06 (q, 1H, $^3J_{HH}$=7.3 Hz, Pn&(H)), 2.12 2.12 2.08 2.07 1.98 1.98 1.90 1.69 1.67 (overlapping s, 3H each, CH$_3$-Pn*(H)), 1.50 1.45 1.44 1.41 (overlapping d, 9H $^3J_{HH}$=6.4 Hz, CHMe), 1.12 (d, 3H, $^3J_{HH}$=7.3 Hz, 1-CH$_3$-Pn*(H)). $^{13}$C{$^1$H} NMR (benzene-d$_6$, 23° C.): Mixture of diastereomers: δ 148.7 142.7 135.5 133.3 (q-Pn*(H)), 128.4 (3,5-C$_6$H$_5$), 127.3 (q-Pn*(H)), 126.9 (2,6-C$_6$H$_5$), 125.6 (4-C$_6$H$_5$), 122.0 116.4 111.4 (q-Pn*(H)), 77.0 (CHMe), 43.3 (1-Pn*(H)), 28.4 (CHMe), 16.1 (1-CH$_3$-Pn*(H)), 12.2 11.8 11.7 11.2 10.6 (CH$_3$-Pn*(H)). Values reported in the $^{13}$C{$^1$H} NMR spectrum are the central values of the multiple overlapping resonances observed.

EXAMPLE 17

Synthesis of η$^5$-Pn*(H)Zr(O-2,6-Me-C$_6$H$_3$)$_3$

[Pn*(H)ZrCl$_3$]$_2$ and KO-2,6-Me$_2$C$_6$H$_3$ were combined in benzene (5 mL) and stirred for 10 minutes to afford a clear, pale-yellow solution and colourless precipitate. Filtration followed by drying of the filtrate in vacuo afforded Pn*(H)Zr(O-2,6-Me-C$_6$H$_3$)$_3$, as a pale-yellow powder. $^1$H NMR (benzene-d$_6$, 23° C.): δ 6.93 (d, 6H, $^3J_{HH}$=7.4 Hz, 3,5-C$_6$H$_3$), 6.75 (t, 3H, $^3J_{HH}$=7.3 Hz, 4-C$_6$H$_3$, 3.31 (q, $^3J_{HH}$=7.4 Hz, Pn*(H)), 2.25 (s, 18H, O-2,6-CH$_3$—C$_6$H$_3$), 2.20 2.12 1.96 1.69 1.54 (s, 3H each, CH$_3$-Pn*(H)), 10.9 (d, 3H, $^3J_{HH}$=7.4 Hz, 1-CH$_3$-Pn*(H)). $^{13}$C{$^1$H} NMR (benzene-d$_6$, 23° C.): δ 159.7 (1-C$_6$H$_3$), 145.3 139.7 135.6 (q-Pn*(H)), 128.9 (3,5-C$_6$H$_3$), 128.0 (q-Pn*(H)), 126.6 (2,6-C$_6$H$_3$), 125.7 (q-Pn*(H)), 120.4 (4-C$_6$H$_3$), 119.0 113.7 (q-Pn*(H)), 43.9 (q-Pn*(H)), 17.9 (O-2,6-CH$_3$—C$_6$H$_3$), 15.7 (1-CH$_3$-Pn*(H)), 12.5 11.8 11.7 11.0 (CH$_3$-Pn*(H)).

EXAMPLE 18

Synthesis of η$^5$-Pn*(H)Zr(O-2,6-$^i$Pr-C$_6$H$_3$)$_3$

[Pn*(H)ZrCl$_3$]$_2$(0.174 g, 0.225 mmol) and KO-2,6-$^i$Pr$_2$C$_6$H$_3$ (0.2925 g, 1.35 mmol) were combined in benzene (5 mL) and stirred for 10 minutes to afford a clear, pale-yellow solution and colourless precipitate. Filtration followed by drying of the filtrate in vacuo afforded η$^5$-Pn*(H)Zr(O-2,6$^i$Pr—C$_6$H$_3$)$_3$, as a yellow-green powder. Anal. Calcd for C$_{50}$H$_{70}$O$_3$Zr: C, 74.11; H, 8.71. Found: C, 67.68; H, 8.60. $^1$H NMR (benzene-d$_6$, 23° C.): δ 7.11-7.03 (overlapping d, 6H, 3,5-C$_6$H$_3$), 6.96 (app. t, 3H, $^3J_{HH}$=6.7 Hz, 4-C$_6$H$_3$), 3.52 (overlapping sept., 6H $^3J_{HH}$=6.7 Hz, CH(CH$_3$)$_2$), 3.11 (q, 1H, $^3J_{HH}$=7.4 Hz, Pn*(H)), 2.17 2.13 1.93 1.85 1.44 (s, 3H each, CH$_3$-Pn*(H)), 1.32 (d, 12H, $^3J_{HH}$=6.7 Hz, CH(CH$_3$)$_2$, 1.01 (d, 3H, $^3J_{HH}$=7.4 Hz, 1-CH$_3$-Pn*(H)). $^{13}$C{$^1$H} NMR (benzene-d$_6$, 23° C.): δ 155.9 155.8 (1-C$_6$H$_3$), 146.8 (q-Pn*(H)), 140.6 (q-Pn*(H)), 137.9 137.7 (2,6-C$_6$H$_3$), 136.4 127.4 (q-Pn*(H)), 123.6 123.5 (3,5-C$_6$H$_3$), 122.1 122.1 (4-C$_6$H$_3$) 120.5 116.2 (q-Pn*(H)), 43.3 (1-Pn*(H)), 27.3 27.2 (CH(CH$_3$)$_2$), 24.9 24.8 24.0 23.9 (CH(CH$_3$)$_2$), 15.6 (1-CH$_3$-Pn*(H)), 12.1 12.0 12.0 11.8 10.9 (CH$_3$-Pn*(H)). One quaternary resonance accounting for a Pn*(H) carbon was overlapping with the residual protio solvent resonance.

EXAMPLE 19

Synthesis of η$^5$-Pn*(H)ZrCl$_2$(O-2,6-$^t$Bu-C$_6$H$_3$)

[Pn*(H)ZrCl3]2 (0.239 g, 0.310 mmol) and KO-2,6-$^t$Bu$_2$C$_6$H$_3$ (0.152 g, 0.62 mmol) were combined in benzene (5 mL) and stirred for 10 minutes to afford a clear, pale-yellow solution and colourless precipitate. Filtration followed by drying of the filtrate in vacuo afforded η$^5$-Pn*(H)ZrCl$_2$(O-2,6-$^t$Bu-C$_6$H$_3$), as a yellow-green powder. Yield: 0.072 g (42%). $^1$H NMR (benzene-d$_6$, 23° C.): δ 7.13 (d, 2H, $^3J_{HH}$=7.7 Hz, 3,5-C$_6$H$_3$), 6.78 (t, 1H, $^3J_{HH}$=7.7 Hz, 4-C$_6$H$_3$), 2.96 (q, 1H, $^3J_{HH}$=7.4 Hz, Pn*(H)), 2.20 2.05 1.98 1.69 (s, 3H each, CH$_3$-Pn*(H)), 1.41 (br. s, 18H, C(CH$_3$)$_3$), 1.32 (s, 3H, CH$_3$-Pn*(H)), 0.86 (d, 6H, $^3J_{HH}$=7.4 Hz, CH(CH$_3$)$_2$). $^{13}$C{$^1$H} NMR (benzene-d$_6$, 23° C.): δ 161.0 (1-C$_6$H$_3$), 148.2 145.9 134.4 132.3 (q-Pn*(H)), 125.4 (3,5-C$_6$H$_3$), 125.2 (q-Pn*(H)), 121.4 (4-C$_6$H$_3$), 119.6 (q-Pn*(H)), 44.7 (1-Pn*(H)), 35.6 (C(CH$_3$)$_3$), 32.1 (C(CH$_3$)$_3$), 15.5 (1-CH$_3$-Pn*(H)), 14.0 12.9 12.4 12.4 116 (CH$_3$-Pn*(H)). Two quaternary resonances accounting for the 2,6-C$_6$H$_3$ and a Pn*(H) carbon were overlapping with the residual protio solvent resonance.

EXAMPLE 20

Synthesis of η$^5$-Pn*(H)Hf(O-2,6-Me-C$_6$H$_3$)$_3$

[Pn*(H)HfCl$_3$]$_2$ and KO-2,6-Me$_2$C$_6$H$_3$ were combined in benzene (5 mL) and stirred for 10 minutes to afford a clear, pale-yellow solution and colourless precipitate. Filtration followed by drying of the filtrate in vacuo afforded Pn*(H)Hf(O-2,6-Me-$C_6H_3$)$_3$, as a pale-yellow powder. $^1$H NMR (benzene-$d_6$, 23° C.): δ 6.93 (d, 6H, $^3J_{HH}$=7.4 Hz, 3,5-$C_6H_3$), 6.74 (t, 3H, $^3J_{HH}$=7.4 Hz, 4-$C_6H_3$), 3.27 (q, 1H, $^3J_{HH}$=7.4 Hz, 4-$C_6H_3$), 3.27 (q, 1H, $^3J_{HH}$=7.4 Hz, Pn*(H)), 2.24 (s, 18H, O-2,6-$CH_3$—$C_6H_3$), 2.24 2.16 1.99 1.68 1.56 (s, 3H each, $CH_3$-Pn*(H)), 1.10 (d, 3H, $^3J_{HH}$=7.4 Hz, 1-$CH_3$-Pn*(H)). $^{13}C\{^1H\}$ NMR (benzene-$d_6$, 23° C.): δ 159.4 (1-$C_6H_3$), 145.1138.7 134.0 (q-Pn*(H)), 129.0 (3,5-$C_6H_3$), 127.8 (q-Pn*(H)), 126.9 (2,6-$C_6H_3$), 124.1 (q-Pn*(H)), 120.4 (4-$C_6H_3$), 117.6 112.1 (q-Pn*(H)), 43.9 (1-Pn*(H)), 17.8 (O-2,6-$CH_3$—$C_6H_3$), 15.5 (1-$CH_3$-Pn*(H)), 12.4 11.8 11.6 11.4 10.9 ($CH_3$-Pn*(H)).

EXAMPLE 21

Synthesis of η$^5$-Pn*(H)HfCl(O-2,6-$^i$Pr-$C_6H_3$)$_2$

[Pn*(H)HfCl$_3$]$_2$ and KO-2,6-$^i$Pr$_2C_6H_3$ were combined in benzene (5 mL) and stirred for 10 minutes to afford a clear, pale-yellow solution and colourless precipitate. Filtration followed by drying of the filtrate in vacuo afforded η$^5$-Pn*(H)HfCl(O-2,6-$^i$Pr-$C_6H_3$)$_2$, as a pale-yellow powder. $^1$H NMR (benzene-$d_6$, 23° C.): δ 7.10-6.86 (overlapping m, 6H, 3,4,5-$C_6H_3$), 3.52 (overlapping sept., 4H, CH($CH_3$)$_2$), 3.11 (q, 1H, $^3J_{HH}$=7.4 Hz, Pn*(H)), 2.25 2.20 1.92 1.92 1.49 (s, 3H each, $CH_3$—Pn*(H)), 1.30 (d, 12H, $^3J_{HH}$=6.5 Hz, CH($CH_3$)$_2$), 1.24 1.23 (overlapping d, 6H each, $^3J_{HH}$=6.5 Hz, CH($CH_3$)$_2$) 1.05 (d, 3H, $^3J_{HH}$=7.4 Hz, 1-$CH_3$-Pn*(H)). $^{13}C\{^1H\}$ NMR (benzene-$d_6$, 23° C.): δ 155.7 155.6 (1-$C_6H_3$), 146.3 139.1 (q-Pn*(H)), 137.9 137.8 (2,6-$C_6H_3$), 134.7 127.6 125.6 (q-Pn*(H)), 123.9 123.5 (3,5-$C_6H_3$), 122.1 122.0 (4-$C_6H_3$), 118.5 114.5 (q-Pn*(H)), 43.5 (1-Pn*(H)), 27.1 27.0 (CH($CH_3$)$_2$), 24.9 24.9 24.1 24.0 (CH($CH_3$)$_2$), 15.5 (1-$CH_3$-Pn*(H)), 11.9 11.8 10.8 ($CH_3$-Pn*(H)).

EXAMPLE 22

Synthesis of η$^5$-Pn*(H)HfCl$_2$(O-2,6-$^t$Bu-$C_6H_3$)

[Pn*(H)HfCl$_3$]$_2$ and KO-2,6-$^t$Bu-$C_6H_3$ were combined in benzene (5 mL) and stirred for 10 minutes to afford a clear, pale-yellow solution and colourless precipitate. η$^5$-Pn*(H)HfCl$_2$(O-2,6-$^t$Bu-$C_6H_3$), was identified as the sole product by NMR spectroscopy. NMR yield: (99.5%). $^1$H NMR (benzene-$d_6$, 23° C.): δ 7.19 (d, 2H, $^3J_{HH}$=7.7 Hz, 3,5-$C_6H_3$), 6.80 (t, 1H, $^3J_{HH}$=7.7 Hz, 4-$C_6H_3$), 2.95 (q, 1H, $^3J_{HH}$=7.4 Hz, Pn*(H)), 2.29 2.16 2.06 1.71 (s, 3H each, $CH_3$-Pn*(H)), 1.42 and 1.44 (br. overlapping s, 18H, C($CH_3$)$_3$), 1.36 (s, 3H, $CH_3$-Pn*(H)), 0.91 (d, 3H, $^3J_{HH}$=7.4 Hz 1-$CH_3$-Pn*(H)). $^{13}C\{^1H\}$ NMR (benzene-$d_6$, 23° C.): δ 160.7 (1-$C_6H_3$), 147.5 143.3 133.0 129.6 127.6 (q-Pn*(H) or 2,6-$CH_3$), 125.4 (3,5-$C_6H_3$), 123.0 (q-Pn*(H) or 2,6-$C_6H_3$), 121.2 (4-$C_6H_3$), 117.7 (q-Pn*(H) or 2,6-$C_6H_3$), 44.5 (1-Pn*(H)), 35.6 (C($CH_3$)$_3$), 32.1 (C($CH_3$)$_3$), 15.5 (1-$CH_3$-Pn*(H)), 13.7, 12.6 12.0 11.4 ($CH_3$-Pn*(H)). One quaternary resonance accounting for either the 2,6-$C_6H_3$ or a Pn*(H) carbon was overlapping with the residual solvent resonance.

Experimental Detail III—Relating to Indenyl-Base Catalysts

General Details

Air and moisture sensitive compounds were manipulated under an inert atmosphere of nitrogen, using standard Schlenk line techniques on a dual manifold vacuum/nitrogen line or a Braun Unilab glove box. Reaction solvents (pentane, hexane, and toluene) were dried using an MBraun SPS-800 solvent purification system. Hexane, toluene, and pentane were stored over pre-activated 3 Å molecular sieves. Dry solvents were stored in oven-dried ampoules under an atmosphere of nitrogen, sealed with either Rotoflo or Young's taps. Deuterated solvents used in NMR analysis of air-sensitive compounds were dried over the appropriate drying agent, freeze-thaw degassed and vacuum transferred prior to use: chloroform-$d_1$ (Sigma-Aldrich) was stored over pre-activated 3 Å molecular sieves. NMR spectra were recorded on a 300 MHz Varian Mercury VX-Works spectrometer. $^1$H (300.27 MHz) and $^{13}C\{^1H\}$ (75.50 MHz) spectra were recorded at 25° C. unless otherwise stated, and referenced internally to the residual protio-solvent peak in the deuterated solvent used. $^1$H and $^{13}C\{^1H\}$ chemical shifts, δ, are given in parts per million (ppm), are given relative to the residual solvent peaks. Air sensitive samples were prepared under an inert atmosphere in a glove box, using dried solvents in Young's taps NMR tubes. [(Ind)$_2$ZrMe$_2$], and complex were synthesised according to literature procedures. [(EBI)ZrCl$_2$] (Strem Chemicals) was hot re-crystallised in toluene.

Polymerisation Procedure

All polymerisations were carried out in Young's tap NMR tubes containing 40 mg of lactide in a chloroform-$d_1$ solution of initiator (20 mg initiator in 4 mL chloroform-$d_1$), ensuring that the lactide:initiator ratio was 50:1. chloroform-$d_1$ was then added to ensure the initial lactide concentration was [LA]$_0$=0.50 M. Polymerisations involving addition tert-butanol were prepared as usual, and tert-butanol was added to the chloroform-$d_1$ solution via microsyringe, ensuring the lactide:initiator:tert-butanol ratio was 50:1:1.

X-Ray Crystallography

Crystals were mounted on MiTeGen MicroMants using perfluoropolyether oil, and cooled rapidly to 150 K in a stream of cold nitrogen using an Oxford Cryosystems CRYOSTREAM unit. Data collections were performed using an Enraf-Nonius FR590 KappaCCD diffractometer, utilising graphite-monochromated Mo K$_\alpha$ X-ray radiation (λ=0.71073 Å). Raw frame data were collected at 150(2) K using a Nonius KappaCCD diffractometer, reduced using DENZO-SMN and corrected for absorption using SORTAV. The structure was solved using SuperFlip and refined using full matrix least-squares using CRYSTALS.

Crystallographic Data of [(EBI)Zr(O-2,6-Me-$C_6H_3$)Cl]

Single crystals were grown from a toluene solution at room temperature, $C_2H_{25}$BCIOZr, $M_r$=504.17, orthorhombic, Pcab, a=15.7733(2) Å, b=23.7683(3) Å, c=23.9207(4) Å, α=90°, β=900, γ=90°, V=8968.0(2) Å$^3$, Z=6, T=150 K, block, yellow, 10201 independent reflections, R(int)=0.070, R$_1$=0.057 wR$_2$=0.137 [I>2σ(I)].

EXAMPLE 23

Synthesis of [(EBI)Zr(O-2,6-Me-$C_6H_3$)Cl]

To one equivalent of [(EBI)ZrCl$_2$] (100 mg, 0.24 mmol) in toluene (10 mL), one equivalent of 2,6-dimethylphenol (29 mg, 0.24 mmol) in toluene (10 mL) was added at room temperature. The yellow suspension was left stirring for 18 h, resulting in a clear, yellow solution. Solvent was removed in vacuo to afford [(EBI)Zr(O-2,6-Me-$C_6H_3$)Cl], as a yellow crystalline solid with a yield of 80% (96 mg, 0.19 mmol). $^1$H NMR (chloroform-d₁, 25° C., 300 MHz): δ 7.84 (1H, dd, ArH, $^3J_{HH}$=8.7 Hz, $^4J_{HH}$=0.9 Hz), 7.61 (1H, dd, ArH, $^3J_{HH}$=8.6 Hz, $^4J_{HH}$=0.9 Hz), 7.30-7.27 (2H, m, ArH), 7.20-7.10 (2H, m, ArH), 7.03 (1H, t, ArMe₂H, $^3J_{HH}$=7.5 Hz), 6.78 (2H, d, ArMe₂H, $^3J_{HH}$=7.4 Hz), 6.63-6.55 (2H, m, ArH), 6.54 (1H, d, CpH, $^3J_{HH}$=3.2 Hz), 6.41 (1H, d, CpH, $^3J_{HH}$=3.2 Hz), 6.15 (1H, d, CpH, $^3J_{HH}$=3.2 Hz), 6.02 (1H, d, CpH, $^3J_{HH}$=3.2 Hz), 3.88-3.62 (4H, m, bridge), 1.91 (6H, s, ArMe₂). $^{13}C\{^1H\}$ NMR (chloroform-d₁, 25° C., 75.5 Mhz): δ 128.2, 126.6, 125.7 125.6, 125.4, 123.7, 123.6, 122.7 121.7, 120.9, 119.5, 115.7, 113.2, 108.4, 106.1 (all non-quaternary ring carbons) 29.6 (C₂H₄), 28.7 (C₂H₄), 18.0 (2×ArMe₂). Quaternary carbons unassigned.

EXAMPLE 24

Synthesis of [Ind₂Zr(O-2,6-Me-C₆H₃)Me]

To one equivalent of [Ind₂ZrMe₂] (100 mg, 0.28 mmol) in toluene (5 mL), one equivalent of 2,6-dimethylphenol (34 mg, 0.28 mmol) in toluene (5 mL) was added at room temperature. The clear, straw-coloured solution was left stirring for 18 h. Solvent was removed in vacuum to afford [(Ind)₂Zr(O-2,6-Me-C₆H₃)Me], as a colourless oil with a yield of 75% (0.21 mmol, 96 mg). ¹H NMR (chloroform-d₁, 25° C., 300 Mhz): δ 7.48-7.43 (2H, m, ArH), 7.34-7.29 (2H, m, ArH), 7.07-7.00 (2H, m, ArH), 6.92-6.85 (2H, m, ArH), 6.82 (2H, d, ArMe₂H, $^3J_{HH}$=7.4 Hz), 6.59 (1H, t, ArMe₂H, $^3J_{HH}$=7.4 Hz), 6.20 (2H, m, CpH), 5.91 (2H, m, CpH), 5.76 (2H, t, CpH, $^3J_{HH}$=3.4 Hz), 1.86 (6H, s, ArMe₂), 0.22 (3H, s, ZrMe). $^{13}C\{^1H\}$ NMR (chloroform-d₁, 25° C., 75.5 Mhz): δ 159.4 (CO, Ar), 128.0 (2×CH, Ar), 125.7 (2×C quaternary, Ar), 124.6 (2×CH, Ar), 124.3 (2×CH, Ar), 124.0 (2×C quaternary, Ar), 123.9 (2×CH, Ar), 123.8 (2×C quaternary, Ar), 123.6 (2×CH, Ar), 118.9 (CH, Ar), 117.6 (2×CH, Cp), 100.6 (2×CH, Cp), 99.0 (2×CH, Cp), 27.8 (ZrMe), 17.6 (2×ArMe₂).

Examples—Polymerisation of Lactides (I)
Polymerisation of L- and Rac-Lactide
L- and Rac-Lactide Monomers

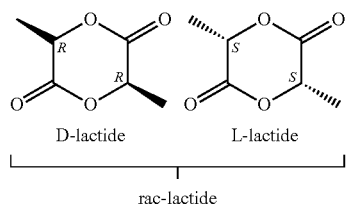

To study the difference between the aryloxide group, pseudo-first order kinetic data of the polymerisation of lactide monomers were carried out with a monomer:initiator ratio of 50 at 100° C. in chloroform-d₁. The results are shown in Table 1 and illustrated in FIG. 1. The observed propagation rates, $k_{obs}$, were determined by analysis of a semi-logarithmic plot of $\ln([LA]_0/[LA]_t)$ vs. time, where $[LA]_0$=0.50 mol/L.

TABLE 1

L-lactide polymerisation: Variation of the aryloxide substituted

| Complex | T (° C.) | $k_{obs}$ (h⁻¹) | $M_n$ (g · mol) | $M_w/M_n$ |
|---|---|---|---|---|
| 2 | 100 | 0.113 ± 0.014 | — | — |
| 7 | 100 | 0.479 ± 0.032 | — | — |
| 8 | 100 | 0.391 ± 0.022 | 7,547 | 1.74 |
| 9 | 100 | 0.043 ± 0.003 | — | — |
| 10 | 100 | 0.364 ± 0.027 | 9,176 | 1.45 |
| 11 | 100 | 0.463 ± 0.029 | 11,680 | 1.60 |
| 12 | 100 | 0.086 ± 0.020 | 7,669 | 1.53 |

Polymerisation conditions: 100° C., [LA]₀ = 50, [LA]₀ = 0.5M, chloroform-d₁.

FIG. 1 illustrates L-lactide polymerisation using the complexes: [η⁵-Pn*(H)Ti(O-2,6-Me-C₆H₃)₃, 2 (black square, $k_{obs}$=0.113±0.014 h⁻¹), η⁵-Pn*(H)Zr(O-2,6-Me-C₆H₃)₃, 7 (red circle, $k_{obs}$=0.479±0.032 h⁻¹), η⁵-Pn*(H)Zr(O-2,6-$^i$Pr-C₆H₃)₃, 8 (pink triangle, $k_{obs}$=0.391±0.022 h⁻¹), η⁵-Pn*(H)ZrCl₂(O-2,6-$^t$Bu-C₆H₃), 9 (dark blue triangle, $k_{obs}$=0.043±0.003 h⁻¹), η⁵-Pn*(H)Hf(O-2,6-Me-C₆H₃)₃, 10 (blue triangle, $k_{obs}$=0.364±0.027 h⁻¹), η⁵-Pn*(H)HfCl(O-2,6$^i$Pr—C₆H₃)₂, 11 (green losange, $k_{obs}$=0.463±0.029 h⁻¹) and η⁵-Pn*(H)HfCl₂( )-2,6$^t$Bu-C₆H₃), 12 (purple triangle, $k_{obs}$=0.086±0.020 h⁻¹). Polymerisation conditions:chloroform-d₁ at 100° C. with [LA]₀/[M]₀=50, [LA]₀=0.5 M.

As can be seen in FIG. 1, the four complexes based on dimethyl and diisopropyl aromatic group with zirconium and hafnium (7, 8, 10 and 11) led to the highest constant of propagation (0.364<$k_{obs}$<0.479 h⁻¹). Both tert-butyl complexes (9 and 12) demonstrated the lowest rate of polymerisation (with $k_{obs}$ of 0.043 h⁻¹ for η⁵-Pn*(H)ZrCl₂(O-2,6-$^t$Bu-C₆H₃) and $k_{obs}$ of 0.086 h⁻¹ for η⁵-Pn*(H)HfCl₂(O-2,6-$^t$Bu-C₆H₃)). When varying the metal using dimethylphenoxide type complexes, it appears that zirconium is faster than hafnium than titanium ($k_{obs}$ of 0.479, 0.391 and 0.113 h⁻¹ respectively). These rates are within the literature range.

The polydispersities are relatively high (1.45<$M_w/M_n$<1.74) certainly due to high temperature of polymerisation. The molecular weights are slightly higher than the theoretical ones (7,547<Mn<11,680 g/mol).

The effect of variation of the alkoxide group substituent on the polymerisation of L-lactide has been studied at 100° C., with a monomer:initiator: ratio of 50 in chloroform-d₁. When complexes η⁵-Pn*(H)Ti(O$^t$Bu)₃, 1, and η⁵-Pn*(H)Zr(O$^t$Bu)₃ 3, were used no conversion was achieved after 1 h. However, changing the tert-butyl group for a benzylic type substituent dramatically increased the rate of the polymerisation with conversion above 90% for η⁵-Pn*(H)Ti(O—CH₂Ph)₃, 4, η⁵-Pn*(H)Zr(O—S—CH{CH₃}C₆H₅)₃, 5, η⁵-Pn*(H)Zr(O-rac-CH{CH₃}C₆H₅)₃, 6, (93, 96 and 97% respectively).

To study the effect of the chirality on the initiating group, pseudo-first order kinetic data of the polymerisation of lactide monomers were carried out with a monomer:initiator: ratio of 50 at 100° C. in chloroform-d₁. The results are shown in Table 2 and illustrated in FIGS. 2-3 and SI.

| Complex | T (° C.) | LA | $k_{obs}$ (h⁻¹) | $M_n$ (g/mol) | $M_w/M_n$ |
|---|---|---|---|---|---|
| 5 | 100 | L- | 3.319 ± 0.754 | 4,549 | 1.37 |
| 6 | 100 | L- | 3.442 ± 0.000 | 4,313 | 1.37 |
| 5 | 100 | rac- | 1.885 ± 0.268 | 3,056 | 1.44 |
| 6 | 100 | rac- | 2.782 ± 0.168 | 2,693 | 1.36 |

-continued

| Complex | T (° C.) | LA | $k_{obs}$ (h$^{-1}$) | $M_n$ (g/mol) | $M_w/M_n$ |
|---|---|---|---|---|---|
| 5 | 80 | L- | 1.166 ± 0.068 | 3,993 | 1.15 |
| 6 | 80 | L- | 1.954 ± 0.063 | 4,106 | 1.18 |
| 5 | 80 | rac- | 1.342 ± 0.055 | 3,109 | 1.18 |
| 6 | 80 | rac- | 1.667 ± 0.053 | 3,856 | 1.24 |
| 5 | 60 | L- | 0.484 ± 0.037 | — | — |
| 6 | 60 | L- | 0.850 ± 0.063 | — | — |
| 5 | 60 | rac- | 0.491 ± 0.031 | — | — |
| 6 | 60 | rac- | 0.767 ± 0.037 | — | — |

Polymerisation conditions: [LA]$_0$/[M]$_0$ = 50, [LA]$_0$ = 0.5M, chloroform-d$_1$.

FIG. 2 shows lactide polymerisation: L-lactide and η$^5$-Pn*(H)Zr(O—S—CH{CH$_3$}C$_6$H$_5$)$_3$, 5 (black square, $k_{obs}$=1.166±0.068 h$^{-1}$); L-lactide and η$^5$-Pn*(H)Zr(O-rac-CH{CH$_3$}C$_6$H$_5$)$_3$, 6 (red circle, $k_{obs}$=1.954±0.063 h$^{-1}$); rac-lactide and η$^5$-Pn*(H)Zr(O-rac-CH{CH$_3$}C$_6$H$_5$)$_3$, 6 (pink triangle, $k_{obs}$=1.667±0.053 h$^{-1}$); rac-lactide and η$^5$-Pn*(H)Zr(O—S—CH{CH$_3$}C$_6$H$_5$)$_3$, 5 (blue triangle, $k_{obs}$=1.342±0.055 h$^{-1}$). Polymerisation conditions:chloroform-d$_1$ at 80° C. with [LA]$_0$/[M]$_0$=50, [LA]$_0$=0.5 M.

FIG. 3 shows lactide polymerisation: L-lactide and η$^5$-Pn*(H)Zr(O—S—CH{CH$_3$}C$_6$H$_5$)$_3$, 5 (black square, $k_{obs}$=0.484±0.037 h$^{-1}$); L-lactide and η$^5$-Pn*(H)Zr(O-rac-CH{CH$_3$}C$_6$H$_5$)$_3$, 6 (red circle, $k_{obs}$=0.850±0.063 h$^{-1}$); rac-lactide and η$^5$-Pn*(H)Zr(O-rac-CH{CH$_3$}C$_6$H$_5$)$_3$, 6 (pink triangle, $k_{obs}$=0.767±0.037 h$^{-1}$); rac-lactide and η$^5$-Pn*(H)Zr(O—S—CH{CH$_3$}C$_6$H$_5$)$_3$, 5 (blue triangle, $k_{obs}$=0.491±0.031 h$^{-1}$). Polymerisation conditions:chloroform-d$_1$ at 60° C. with [LA]$_0$/[M]$_0$=50, [LA]$_0$=0.5 M.

Both complexes η$^5$-Pn*(H)Zr(O—S—CH{CH$_3$}C$_6$H$_5$)$_3$, 5, η$^5$-Pn*(H)Zr(O-rac-CH{CH$_3$}C$_6$H$_5$)$_3$, 6 demonstrated very high rate of polymerisation for L- and rac-lactide (1.885<$k_{obs}$<3.442 h$^{-1}$) at 100° C. Over the three temperatures (60, 80 and 100° C.), the racemic complex polymerised faster both lactide monomers. At 60° C., the observed propagation rates when using rac-η$^5$-Pn*(H)Zr(O—CH{CH$_3$}C$_6$H$_5$)$_3$, 6 are around 70% faster ($k_{obs}$ of 0.850 h$^{-1}$ for L-lactide and 0.767 h$^{-1}$ for rac-lactide) than when η$^5$-Pn*(H)Zr(O—S—CH{CH$_3$}C$_6$H$_5$)$_3$ 5 was used ($k_{obs}$ of 0.484 h$^{-1}$ for L-lactide and 0.491 h$^{-1}$ for rac-lactide). L- and rac-lactide appears to be polymerised at similar rates of polymerisation.

The polydispersities decreased with decreasing temperature (1.27<$M_w/M_n$<1.44 for 100° C. and 1.15<$M_w/M_n$<1.24 for 80° C.). The molecular weight experimental are half of the theoretical (2,693<$M_n$<4,549 g/mol).

The activation parameters for the ring-opening polymerisation of L- and rac-lactide initiated using η$^5$-Pn*(H)Zr(O—S—CH{CH$_3$}C$_6$H$_5$)$_3$, 5, η$^5$-Pn*(H)Zr(O-rac-CH{CH$_3$}CH$_5$)$_3$, 6 were determined using Eyring plots and found to be 30.4<ΔH$^\#$<46.6 kJ/mol and 411.4<ΔS$^\#$<640 J/(mol K), FIG. 4 and SI.

FIG. 4 is an Eyring plot of L-lactide polymerisation using η$^5$-Pn*(H)Zr(O—S—CH{CH$_3$}C$_6$H$_5$)$_3$, 5. Slope=−5610±488 with R$^2$=0.993. Polymerisation conditions: chloroform-d$_1$ with [LA]$_0$/[Zr]=50 and [LA]$_0$=0.5 M.

Pseudo-first order kinetic data of the polymerisation of L-lactide to study the effect of variation of the concentration of the monomer:initiator ratio at 100° C. in chloroform-d$_1$ using η$^5$-Pn*(H)Zr(O-2,6$^i$Pr—C$_6$H$_3$)$_3$, 8. The results are collated in Table 3 and illustrated FIG. 5.

TABLE 3

L-lactide polymerisation: Variation of the concentration

| Complex | [LA]$_0$/[Zr]$_0$ | $k_{obs}$ (h$^{-1}$) | $M_n$ (g/mol) | $M_w/M_n$ |
|---|---|---|---|---|
| 8 | 25 | 0.521 ± 0.021 | 6,920 | 1.72 |
| 8 | 50 | 0.391 ± 0.022 | 7,547 | 1.74 |
| 8 | 100 | 0.377 ± 0.015 | 9,870 | 1.40 |
| 8 | 200 | 0.235 ± 0.004 | 17,042 | 1.54 |

Polymerisation conditions: 100° C., [LA]$_0$ = 0.5M, chloroform-d$_1$.

FIG. 5 shows L-lactide polymerisation using η$^5$-Pn*(H)Zr(O-2,6-Pr—C$_6$H$_3$)$_3$, 8: [LA]$_0$/[Zr]$_0$—25 (black square, $k_{obs}$=0.521±0.021 h$^{-1}$); [LA]$_0$/[Zr]$_0$=50 (red circle, $k_{obs}$=0.391±0.022 h$^{-1}$); [LA]$_0$/[Zr]$_0$=100 (blue triangle, $k_{obs}$=0.377±0.015 h$^{-1}$); [LA]$_0$/[Zr]$_0$=200 (pink triangle, $k_{obs}$=0.235±0.004 h$^{-1}$). Polymerisation conditions:chloroform-d$_1$ at 100° C. with [LA]$_0$=0.5 M.

As expected the rate of the polymerisations of L-lactide at 100° C. in chloroform-d$_1$ increased with decreasing monomer:initiator ratio ($k_{obs}$ of 0.235, 0.377, 0.391 and 0.521 h$^{-1}$ for [LA]$_0$/[Zr]$_0$ of 200, 100, 50 and 25 respectively). Furthermore, the molecular weights, $M_n$, increased with increasing concentration from 6,920 to 17,042 g/mol for initial monomer:initiator ratio of 25 to 200 respectively. The polydispersities, $M_w/M_n$, are varying between 1.40<$M_w/M_n$<1.74.

The observed rate of the propagation of L-lactide using η$^5$-Pn*(H)Zr(O-2,6-Pr—C$_6$H$_3$)$_3$, 8, demonstrated a pseudo first-order kinetic as a function of the initiator (FIG. 6).

FIG. 6 shows a plot of Ln($k_{obs}$) vs Ln([ZR]$_0$) using η$^5$-Pn*(H)Zr(O-2,6-Pr—C$_6$H$_3$)$_3$. 8. Slope=0.350±82 with R$^2$=0.901. Polymerisation conditions: chloroform-d$_1$ at 100° C. and [LA]$_0$=0.5 M.

Pseudo-first order kinetic data of the polymerisation of L-lactide to study the effect of temperature with monomer:initiator ratio of 50 in chloroform-d$_1$ using η$^5$-Pn*(H)Zr(O-2,6-Pr—C$_6$H$_3$)$_3$, 8. The results are collated in Table 4 and illustrated FIG. 7.

TABLE 4

L-lactide polymerisation: Variation of the temperature

| Complex | T (° C.) | $k_{obs}$ (h$^{-1}$) | $M_n$ (g/mol) | $M_w/M_n$ |
|---|---|---|---|---|
| 8 | 100 | 0.391 ± 0.022 | 6,920 | 1.72 |
| 8 | 90 | 0.151 ± 0.008 | 7,751 | 1.59 |
| 8 | 80 | 0.092 ± 0.006 | 6,348 | 1.58 |

Polymerisation conditions: [LA]$_0$/[M]$_0$ = 50, [LA]$_0$ = 0.5M, chloroform-d$_1$.

FIG. 7 shows L-lactide polymerisation using η$^5$-Pn*(H)Zr(O-2,6-Pr—C$_6$H$_3$)$_3$, 8: T=100° C. (black square, $k_{obs}$=0.391±0.022 h$^{-1}$); T=90° C. (red circle, $k_{obs}$=0.151±0.008 h$^{-1}$); T=80° C. (blue triangle, $k_{obs}$=0.092±0.006 h$^{-1}$). Polymerisation conditions: chloroform-d$_1$ with [LA]$_0$[M]$_0$=50, [LA]$_0$—0.5 M.

As expected the rate of the polymerisations of L-lactide in chloroform-d$_1$ decreased with decreasing temperature ($k_{obs}$ of 0.391, 0.151 and 0.092 h$^{-1}$ for T of 100, 90 and 80 respectively). The molecular weights, $M_n$, remain constant between 6,348 to 7,751 g/mol which are very close to the theoretical ones. However, the polydispersities, $M_w/M_n$, decreased with decreasing temperature from 1.72 to 1.58 for 100 to 80° C. respectively.

The activation parameters for the ring-opening polymerisation of L-initiated using η$^5$-Pn*(H)Zr(O-2,6-Pr—C$_6$H$_3$)$_3$, 8 were determined using Eyring plots and found to be ΔH$^{\#}$=75.9 kJ/mol and ΔS$^{\#}$=1847 J/(mol K), FIG. 8.

FIG. 8 shows an Eyring plot of L-lactide polymerisation using η$^5$-Pn*(H)Zr(O-2,6-Pr$_2$C$_6$H$_3$)$_3$, 8. Slope=−9133±1881 with R$^2$=0.959. Polymerisation conditions: chloroform-d$_1$ with [LA]$_0$/[Zr]$_0$=50 and [LA]$_0$=0.5 M.

The synthesized polylactides were characterised by $^1$H, $^1$H{$^1$H} and $^{13}$C{$^1$H} NMR spectroscopy. The NMR spectra demonstrated no epimerisation when L-lactide was polymerised and an isotactic biased PLA when rac-lactide was polymerised.

They have also been characterised by MALDI-TOF and $^{13}$C{$^1$H} NMR spectroscopy to determine the end of chains. It was shown that the lactide monomers inserted in the metal-oxygen bond.

(II)

Pseudo-first order kinetic data of the polymerisation of L-lactide at 80° C. in beneze-d$_6$, with an initiator: monomer ratio of 1:50, using selected permethylpentalene complexes are shown in FIG. 9. The kinetic data for all polymerisations displayed an induction period that varied depending on the initiating complex. As such, the data in FIG. 9 is given from 32 h, by which time all induction periods had ended.

The complex that exhibited by far the highest activity towards the ring-opening polymerisation of lactide isomers was [η$^5$-(Pn*)Ti(O-2,6-Me-C$_6$H$_3$)$_2$]. It demonstrates a rate of polymerisation similar to published titanium complexes (k$_{obs}$=69.9×10$^{-3}$ h$^{-1}$)$^{37}$ and ten times faster than the complexes [η$^8$-(Pn*)Ti(O-2,6-Me-C$_6$H$_3$)Cl] and [η$^8$-(Pn*)Ti(O-2,4-Bu-C$_6$H$_3$)Cl] at 80° C. which demonstrated similar rates of propagation, (k$_{obs}$=7.2×10$^{-3}$ h$^{-1}$ and 7.0×10$^{-3}$ h$^{-1}$ respectively). These rates of propagation being 3.5 times faster than when [η$^5$-(Pn*)Ti(O-2,6-Me-C$_6$H$_3$)Cl$_2$] was used (k$_{obs}$=1.9×10$^{-3}$ h$^{-1}$).

FIG. 9 shows semi-logarithmic plots of L-lactide conversion vs time, [LA]$_0$/[Init]$_0$=50, [LA]$_0$=0.104 M, T=80° C., benzene-d$_6$ (0.5 mL), using [η$^8$-(Pn*)Ti(O-2,6-Me-C$_6$H$_3$)Cl], (green dotted line), [η$^8$-(Pn*)Ti(O-2,4-$^t$Bu-C$_6$H$_3$)Cl], (black dashed line) [η$^8$-(Pn*)Ti(O-2,6-Me-C$_6$H$_3$)$_2$] (red line) and [η$^5$-(Pn*H)Ti(O-2,6-Me-C$_6$H$_3$)Cl$_2$] (blue dot-dashed line). Induction period omitted.

As is shown in FIG. 10, at 90° C., when initiated by [η$^8$-(Pn*)Ti(O-2,6-Me-C$_8$H$_3$)$_2$], rac- and L-lactide polymerise at the same rate (k$_{obs}$≈110×10$^{-3}$ h$^{-1}$). This is presumably because the achiral initiator cannot distinguish between both lactide enantiomers and has incorporated each at the same rate. This absence of stereochemical preference suggests that the polymerisation goes by a chain-end controlled mechanism.

FIG. 10 shows semi-logarithmic plots of lactide monomers conversion vs time. Induction period omitted. [LA]$_0$=0.104 M, [LA]$_0$/[Init]$_0$=50, T=90° C., benzene-d$_6$. Polymerisation using [η$^8$-(Pn*)Ti(O-2,6-Me-C$_6$H$_3$)$_2$], L-lactide (red line) and rac-lactide (black dashed line).

Polymerisations of L-lactide using [η$^8$-(Pn*)Ti(O-2,6-Me-C$_6$H$_3$)$_2$] were carried out in the temperature range of 80 to 100° C. and the results were collated to an Eyring plot. From the Eyring plot an estimation of the activation parameters were obtained: ΔH$^{\#}$=75.15 kJ mol$^{-1}$, ΔS$^{\#}$=−125.85 J K$^{-1}$ mol$^{-1}$, ΔG$^{\#}$ (100° C.)=87.74 kJ mol$^{-1}$. The modest value of ΔH$^{\#}$ is typical for attack on a carbonyl group coordinated to a metal centre and the negative and relatively high value of ΔS$^{\#}$ implies a high degree of order in the transition state. As such, all parameters are consistent with a coordination insertion mechanism displaying a highly ordered transition state. The polymerisation of L-lactide leads to isotactic PLA and rac-lactide to atactic PLA.

(III)

Pseudo-first order kinetic data of the polymerisation of L-lactide using [(EBI)Zr(O-2,6-Me-C$_6$H$_3$)Cl], [(Ind)$_2$Zr(O$^t$Bu)Me], and [(Ind)$_2$Zr(O-2,6-Me-C$_6$H$_3$)Me] are shown in FIG. 11. All initial polymerisation studies were carried out at 80° C. in chloroform-d$_1$, with an L-LA:initiator ratio of 50:1, ensuring [LA]$_0$—0.50 M.

FIG. 12 shows semi-logarithmic plots of L-lactide conversion vs time, [LA]$_0$/[Init]$_0$=50, [LA]$_0$=0.50 M, T=80° C., chloroform-d$^1$ (0.5 mL), polymerisation using [(EBI)Zr(O-2,6-Me-C$_6$H$_3$)Cl], (dotted line), [(Ind)$_2$Zr(O$^t$Bu)Me], (solid line), [(Ind)$_2$Zr(O-2,6-Me-C$_6$H$_3$)Me], (dashed line). FIG. 12 shows that complex [(Ind)$_2$Zr(O$^t$Bu)Me] displayed the highest activity with 84% conversion in eight hours (k$_{obs}$=0.24 h$^{-1}$) and no initiation period. This is comparable to moderate activities of zirconium initiators in the literature. A significantly lower activity was displayed by [(Ind)$_2$Zr(O-2,6-Me-C$_6$H$_3$)Me] which achieved 74% conversion after 28 h (k$_{obs}$=0.05 h$^{-1}$), at a rate 4.5 times slower than [(Ind)$_2$Zr(O$^t$Bu)Me]. Interestingly, [(Ind)$_2$Zr(O-2,6-Me-C$_6$H$_3$)Me] displayed an initiation period of around half an hour. These observations are rationalised by the increased bulk of the aryl-oxide substituent of [(Ind)$_2$Zr(O-2,6-Me-C$_6$H$_3$)Me] compared to the tert-butoxide substituent of [(Ind)$_2$Zr(O$^t$Bu)Me]. In comparison, [(EBI)Zr(O-2,6-Me-C$_6$H$_3$)Cl]exhibited the lowest catalytic activity, managing 4.2% conversion in 28 h (k$_{obs}$=0.002 h$^{-1}$) which is comparable to rac-[(EBI)Zr(OC{O$^i$Pr}=CMe$_2$)] (7% conversion in 18 h at 80° C. in toluene) synthesised by Ning et al, Organometallics, 2008, 27, 5632. The rate of [(EBI)Zr(O-2,6-Me-C$_6$H$_3$)Cl] is two orders of magnitude less than [(Ind)$_2$Zr(O$^t$Bu)Me] and [(Ind)$_2$Zr(O-2,6-Me-C$_6$H$_3$)Me], probably due to both the increased bulk of the arylxoxide compared to the tert-butoxide and the increased rigidity conferred by the ansa-bridged ligand, preventing reorientation of the indenyl moieties.

As [(Ind)$_2$Zr(O$^t$Bu)Me] showed the highest rate of polymerisation, further studies were carried out to investigate its stereoselectivity and estimate its activation. Polymerisations using [(Ind)$_2$Zr(O$^t$Bu)Me] as the initiator were carried out between 60° C. and 100° C., with the same LA:initiator ratios and [LA]$_0$ as used previously. The enthalpy of activation (ΔH$^{\ddagger}$) and the entropy of activation (ΔS$^{\ddagger}$) were calculated from a plot of ln(k$_{obs}$/T) vs. (1/T) (FIG. 12), giving ΔH$^{\ddagger}$=46.9 kJ·mol$^{-1}$ and ΔS$^{\ddagger}$=−193.9 J·K$^{-1}$·mol$^{-1}$. These values are consistent with the literature; typical for a bimolecular reaction, and a coordination-insertion mechanism.

Furthermore, it was found that polymerisation of L-LA (k$_{obs}$=0.24 h$^{-1}$) was twice as fast as rac-LA (k$_{obs}$=0.11 h$^{-1}$) with [(Ind)$_2$Zr(O$^t$Bu)Me] at 80° C. with similar [LA]$_0$:[2]$_0$ ratio of 50:1 (FIG. 13). This is probably due to the energy barrier required to invert the chiral configuration at the metal centre, which is indicative of a chain-end control mechanism.

The $^1$H{$^1$H} NMR spectrum of the polymerisation of rac-LA using [(Ind)$_2$Zr(O$^t$Bu)Me] as initiator demonstrated a bias towards isotactic PLA, P$_i$ of 72%.

Polymerisations of L-LA and rac-LA were repeated at 80° C. with the addition of tert-butanol in stoichiometric amounts with [(Ind)$_2$Zr(O$^t$Bu)Me]. The addition of tert-butanol has little effect on k$_{obs}$ for both L-LA and rac-LA. The rate of polymerisation for L-LA without alcohol is similar to the one with (k$_{obs}$ of 0.24 h$^{-1}$ and 0.23 h$^{-1}$ respectively). Similarly the rates for the polymerisations of rac-LA were (k$_{obs}$ of 0.11 h$^{-1}$ and 0.10 h$^{-1}$ respectively). The molecular weights and polydispersities of the polymerisation of L-LA and rac-LA with and without tert-butanol are collated in Table 5. As an initiator, [(Ind)₂Zr(O^tBu)Me] demonstrated highly controlled polymerisation of L-LA and rac-LA at 80° C. with a LA:initiator ratio of 50:1 in chloroform-$d_1$, as shown by low polydispersities (1.08<$M_w$/$M_n$<1.12). The addition of tert-butanol does not affect the polydispersities; however, the experimental molecular weights appear more controlled in the presence of the alcohol, as expected of immortal polymerisation.

TABLE 5

Polymerisation data for L- and rac-lactide using $2^a$

| | Alcohol | $M_{n, theo}$/$M_{n, exp}$ | $M_{n, exp}^b$ (g · mol−1) | $M_w/M_n^b$ |
|---|---|---|---|---|
| rac-La | no | 1.96 | 11171 | 1.08 |
| rac-LA | yes | 0.96 | 5779 | 1.10 |
| S, S-LA | no | 2.19 | 13813 | 1.12 |
| S, S-LA | yes | 1.45 | 9065 | 1.09 |

$^a$Polymerisation conditions; [LA]₀/[2]₀ = 50, [LA]₀ = 0.5M, 80° C.
$^b$Measured by GPC with polystyrene standards in THF. $M_{n, theo}$ = [LA]₀/[2]₀ × $M_{LA}$ × conv.

The invention claimed is:

1. A compound having the formula $L_aM(OR^1)_bR^2_cX_d$ wherein
M is a metal selected from Ti, Zr and Hf;
L is a ligand selected from permethylpentalene, (hydro) permethyl-pentalene, and (hydro)pentalene;
$R^1$ is a 1-6C alkyl, substituted or unsubstituted phenyl, or a substituted or unsubstituted phenylalkylene group;
$R^2$ is Me or Et;
X is halogen;
a=1 to 3, b=1 to 3, c=0 or 1 and d=0, 1, 2 or 3;
or a dimer thereof.

2. The compound according to claim 1, wherein L is permethylpentalene and X is Cl.

3. The compound according to claim 1, wherein $R^1$ is a group selected from —$^tBu$, —$C_6H_3(R^3)_2$, where $R^3$ is 1-4C alkyl, and —CH($R^4$)Ph, where $R^4$ is H or 1-4C alkyl.

4. The compound according to claim 3, wherein $R^1$ is selected from 2,6-dimethylphenyl, 2,6-diisopropylphenyl and 2,6-di$^t$butylphenyl.

5. The compound according to claim 3, wherein $R^4$ is Me.

6. The compound according to claim 1, wherein M is Ti.

7. The compound according to claim 1, wherein M is Zr.

8. The compound according to claim 1, wherein M is Hf.

9. A method for polymerizing a lactide monomer, wherein an initiator in the polymerisation of a lactide monomer is a compound having the formula $L_aM(OR^1)_bR^2_cX_d$ wherein
M is a metal selected from Ti, Zr and Hf;
L is a ligand selected from permethylpentalene, (hydro) permethyl-pentalene, and (hydro)pentalene;
$R^1$ is a 1-6C alkyl, substituted or unsubstituted phenyl, or a substituted or unsubstituted phenylalkylene group;
$R^2$ is Me or Et;
X is halogen;
a=1 to 3, b=1 to 3, c=0 or 1 and d=0, 1, 2 or 3;
or a dimer thereof.

10. The method according to claim 9, wherein the lactide monomer is L-lactide.

11. The method according to claim 9, wherein the lactide monomer is rac-lactide.

12. A process for producing a polylactide which comprises contacting a lactide monomer with a compound having the formula $L_aM(OR^1)_bR^2_cX_d$ wherein
M is a metal selected from Ti, Zr and Hf;
L is a ligand selected from permethylpentalene, (hydro) permethyl-pentalene, and (hydro)pentalene;
$R^1$ is a 1-6C alkyl, substituted or unsubstituted phenyl, or a substituted or unsubstituted phenylalkylene group;
$R^2$ is Me or Et;
X is halogen;
a=1 to 3, b=1 to 3, c=0 or 1 and d=0, 1, 2 or 3;
or a dimer thereof.

13. The process according to claim 12, wherein the lactide monomer is L-lactide and the polylactide is isotactic polylactide.

14. The process according to claim 12, wherein the lactide monomer is rac-lactide and the polylactide is atactic polylactide.

* * * * *